US006291168B1

(12) United States Patent
Musso

(10) Patent No.: US 6,291,168 B1
(45) Date of Patent: Sep. 18, 2001

(54) NUCLEIC ACID SEQUENCES DIAGNOSTIC FOR PATHOGENIC E.COLI O157:H7, METHODS OF IDENTIFICATION AND KIT THEREFORE

(75) Inventor: Richard E. Musso, Auburn, AL (US)

(73) Assignee: Auburn University, AL (US)

( * ) Notice: Subject to any disclaimer, the term of this patent is extended or adjusted under 35 U.S.C. 154(b) by 0 days.

(21) Appl. No.: 09/179,221

(22) Filed: Oct. 27, 1998

(51) Int. Cl.[7] .............................. C12Q 1/68; C12Q 1/44; C12P 19/34; C07H 21/04
(52) U.S. Cl. ................................ 435/6; 435/15; 435/19; 435/91.2; 536/23.1; 536/23.7; 536/24.32; 536/24.33
(58) Field of Search ................................. 435/6, 15, 19, 435/91.2; 536/23.1, 23.7, 24.32, 24.33

(56) References Cited

U.S. PATENT DOCUMENTS 5,756,293 * 5/1998 Hall et al. ............................. 435/6

OTHER PUBLICATIONS

Ronecker, H–J. et al. Gene 59:291–296, 1987.*
Erlich, H.A. et al. Science 252:1643–1650, Jun. 1991.*
Ivanova, A. et al. Nucleic Acids Research 20(20):5479–5480, 1992.*
Venkatesan, M.M. et al. Mol. Microbiol. 5(10):2435–2445, 1991.*
Mulvey, M.R. et al. Nucleic Acids Research 17(23):9979–9991, 1989.*
Prince, R.W. et al. Biochim. Biophys. Acta 1219:198–200, 1994.*
Venkatesan, M.M. et al. Accession No. M76445, Oct. 1991.*
Ronecker, H.J. et al. Accession No. V00279, J01732, M18426, Feb. 1999.*

* cited by examiner

Primary Examiner—Carla J. Myers
Assistant Examiner—Diana Johannsen
(74) Attorney, Agent, or Firm—Schnader Harrison Segal & Lewis LLP

(57) ABSTRACT

This invention relates to diagnostic tests that will specifically identify E. coli O157:H7. Tests are provided to detect E. coli O157:H7 by PCR and by Southern blotting. Methods and primer compositions are provided to identify two distinct and independent regions of the E. coli O157:H7 genome by polymerase chain reaction. Methods and probe compositions are also provided to detect E. coli O157:H7 by Southern blotting. Kits to identify E. coli O157:H7, comprising said primer and probe compositions and reagents to conduct the appropriate control tests, are also provided.

41 Claims, 10 Drawing Sheets

Figure 1

N58
5'  GCTTCGATAT TCAGCCCCTG ATGTTCGCCT TTCTGCACCT GGCTCTTTTG CCCATAAGAT

TAATTTTCCT GTTGAAACGC CCTGTTTTCA GATTAAACAG ACGGAACTGA AGGGGGCTGA

TGCGTTACCA CACTGGCTGC CTTTACAAAA AATCGCCAAC GGGGCGGTCG GGCATTGCCT

GGGGGCGAAA GGAATTAATC TGCTGATGAG TACATTGCAG AACCGTCTGG TCGATCATGG

TTATGTCACC ACCCGTGTTC TGGCACCTTC GCAGGATTTA AAAAGCGGTA TCCTCCGGCT

GGTTATTATT CCCGGTGTTG TGCGACATGT GCGTCTGACA CCGGACAGTG ATGACTATAT

TCAGTTGTAT TCCTCATTCC CGGCACACGA AGGTTCTCTG CTGGATTTAC GGGACATTGA

N58'
    GCAGGGGCTG AATATCGAAG C

Figure 2

```
                                         G
TAGACTGGCC  CCCTGAATCT  CCAGACAACC  AATATCACTT  AAATAAGTGA  TAGTCTTAAT    60
ACTAGTTTTT  AGACTAGTCA  TTGGAGAACA  GATGATTGAT  GTCTTAGGGC  CGGAGAAACG   120
CAGACGGCGT  ACCACACAGG  AAAAGATCGC  AATTGTTCAG  CAGAGCTTTG  AACCGGGGAT   180
GACGGTCTCC  CTCGTTGCCC  GGCAACATGG  TGTAGCAGCC  AGCCAGTTAT  TTCTCTGGCG   240
            T
TAAGCAATAC  CAGGAAGGAA  GTCTTACTGC  TGTCGCCGCC  GGAGAACAGG  TTGTTCCTGC   300
CTCTGAACTT  GCTGCCGCCA  TGAAGCAGAT  TAAAGAACTC  CAGCGCCTGC  TCGGCAAGAA   360
AACGATGGAA  AATGAACTCC  TCAAAGAAGC  CGTTGAATAT  GGACGGGCAA  AAAAGTGGAT   420
AGCGCACGCG  CCCTTATTGC  CCGGGGATGG  GGAGTAAGCT  TAGTCAGCCG  TTGTCTCCGG   480
                    T
GTGTCGCGTG  CGCAGTTGCA  CGTCATTCTC  AGACGAACCG  ATGACTGGAT  GGATGGCCGC   540
CGCAGTCGTC  ACACTGATGA  TACGGATGTG  CTTCTCCGTA  TACACCATGT  TATCGGAGAG   600
      C
CTGCCAACGT  ATGGTTATCG  TCGGGTATGG  GCGCTGCTTC  GCAGACAGGC  AGAACTTGAT   660
GGTATGCCTG  CGATCAATGC  CAAACGTGTT  TACCGGATCA  TGCGCCAGAA  TGCGCTGTTG   720
              A
CTTGAGCGAA  AACCTGCTGT  ACCGCCATCG  AAACGGGCAC  ATACAGGCAG  AGTGGCCGTG   780
AAAGAAAGCA  ATCAGCGATG  GTGCTCTGAC  GGGTTCGAGT  TCTGCTGTGA  TAACGGAGAG   840
                                                          G
AGACTGCGTG  TCACGTTCGC  GCTGGACTGC  TGTGATCGTG  AGGCACTGCA  CTGGGCGGTC   900
ACTACCGGCG  GCTTCAACAG  TCAAACAGTA  CAGGACGTCA  TGCTGGGAGC  GGTGGAACGC   960
CGCTTCGGCA  ACGATCTTCC  GTCGTCTCCA  GTGGAGTGGC  TGACGGATAA  TGGTTCATGC  1020
TACCGGGCTA  ATGAAACACG  CCAGTTCGCC  CGGATGTTGG  GACTGGAACC  GAAGAACACG  1080
                                           A
GCGGTGCGGA  GTCCGGAGAG  TAACGGAATA  GCAGAGAGCT  TCGTGAAAAC  GATAAAGCGT  1140
GACTACATCA  GTATCATGCC  CAAACCAGAC  GGGTTAACGG  CAGCAAAGAA  CCTTGCAGAG  1200
GCGTTCGAGC  ATTATAACGA  ATGGCATCCG  CATAGTGCGC  TGGGTTATCG  CTCGCCACGG  1260
GAATATCTGC  GGCAGCGGGC  TTGTAATGGG  TTAAGTGATA  ACAGATGTCT  GGAAATATAG  1320
GGGCAAATCC  A                                                           1331
```

Figure 3

```
GATGGATTTA TCGTAATAAA GACAACAGCC AAATAATGAA AAACATAAAA TTTTATCTGC

ATGGCAAAGA GATACCAGCA GAAAGAATAT TAGATACACC AGAGTGGAAA GACTACCGTC

CAAAATACTC CGGTTCCACA TATAAATATT CTTAATGATA GCAAAAAATA TATTTTCGAT

ATAATCAATG TTATGATTAA AGAGTATTTC ATCAGGGCAG GTAAAAACAG AGTAAATCAG

CAAAAGAAGC TGATCTTCAG CGATACTGAC ACTAACTGAC GGTTTAAGCG GTCGTATGAA

GCAGCAGCTT TCCGACGGAC TGCCATGCGG ATCGTTTACC TTTTGGGCTA TTCCGCCCGT

CATCAAGCGG CTCACGAGTA CTGAGTTTAT CAGGGATGAT ATTGCTGACA ATGGGTAATT

CGTTGAACCG ATGTGTACTT TCACTACATA TCGGTCAACA CCGGTACTGG CCGTGCAACA

TCTCCCAGAT GTTACATCCG TTTTTACCCN AAGGAGGCGG GACATANAAT GTTAA
```

Figure 4

```
       AACCAA CAATGGTATA AAAATGGGCC ATTCTTAATC CATGCAGGAC GGAATGGGAG
GAAGTATTCG CCAAAAGTTA AATTCAACAG TCTGTTGGTT TTGAGATATA ACTNTCTTTT
CTAATATGGA CACCTTGGCT TTGCTGGTTG TTAAAATTAG CTTGTTGATT AGTAGTATGG
ATAGAACTTA CTCTGTTATT TATTTCTAAA AATGGAATTT ATCAATGCTT CCTACATCGC
AATTACGACC GACCGGGACA TTCTGCTCCT ATTCCGCTGA AACATCAGCA GACATCAAAA
GCGAAATCAC ACCAATTCAG ATAGAAGAAG CGCGGGCCAG TGGTCGTTTA TATATCAAAG
ATTGTGATAT TGAGTATCTG CCACAGTTAC CAAACGAAAT AACATCAGTT ACAATCGAAA
ACTGCAACAA CCTGACAACC CTTACAGGAT TGCCGGTTAA TACACAAAAC CTCTCCGTCA
TTAACTGTGA AAAATTACAA ATCACAGACA TGCCATCAAC CGTAAAAAAT NTACATATTG
AATTAACTGA TTCACCATTT ATACATTTCA TATCTGAAGG CATCGAGTGC CTGACGGTTT
GCCACTGCTA TATATCTGGA GTGCCAGAGA GTGTCCGCTA CCTTGAAATA AAAGGTAGCG
CCACAGACAG CATAAAAATG TTCCAAACGG GTTATCATCT NTCAGCATCA ATAGCTATAA
CCCGGAGAAT CAGGCCAGAA TTGACCACCT GATATCACCG TCACTGAAGA CGCTATCGCT
GACTGGATGT AGCAATATTA TACTGCCGGA GAAACTTCCG GAGAGTGTGA CATCGGTAAC
CATTCATGCG GAGCAGAAAA CCACGTGGAA CATCGGTGTT GAAGGGATGC CTGATGGGCT
GGATCTTGAT TTACAAAATG TACTACTCTC TCCAGATGTA GTTAAAGCAA AAAACATCAC
CTTTCAGGGC AACGCTCTGG ATGTGGCCTT ACACTTTCGC GAGGGAGACA TTGTCTATGG
ACTATCTTCA CCCAGAGAAA AACTTGTCAA CAGCATTAAA CTAGTTAACG ACTTTTCCAA
AAAAGATATT ATAACTCAGA ATACGTTAAC AAACGCAGTA TGGGACCCCA GAACACCTCG
CAAATATAAG CAAGATCCAC TTATCAAAAG AGCATTAAAT GAACACGAAA GAGGAATAAA
ATTTAAACAA CACTTAAGGA ATCACAATAA TTATAATGTT ACCATGGCCG ACCTTTCCGT
ATACAATCGC GACAAATTAT GGGCAAAAAC AAGCAAGGCC GGCCTAGAGT TTCAGACATT
AACACGCAAT AAAACGGTTA TTTTTTGTGC GGATGAGCTT GTCAACTCAC TCAAACTCAT
AGCTAACAAG TCAGAGGGCT ATGGCCAGAG TATTACCGCC AGCGAATTTC GATGGATTTA
***CCGTAATAAA GACAACAGCC AAATAATG**AA AAACATAAAA TTTTATCTAC ATGGCAAAGA
GATACCAGCA GAAAGAATAT TAGATACACC AGAATGGAAA GACTATCGTC CAAAATACTC
TGGTTCCACA TATAAATATT CTTAATGATA CCAACTTATA ACGGAATAGC ATAAAAACAC
TTTTCATGGA GCAAAGGAGA AAACAATGCC ATTTTCAATC AAAAACAGAT TTTCAAGTTC
ACAAGTACAT TACCCGGAAA TATCCGGTCC CATAAAAGAC AAGCCAGCGT CAAAGAACTG
CATACTTACA TCAACAACAT GTAATGTAGA TAGCTATACA GTGTACCAAA AAAAAGCCTG
TAGTTTTGAC ATGCGCCCAC CCGGCGCAGG AGAAAGAACC CCAAAACTAA AACTCTCAGT
TACTGAGATG ACATGGCTAT CTAAAACTAT AGAAACAGAG ATACACAACA CAAAAGAATA
GCAACCACTT ACCAGAGAAC ACAAAAAGCC ACAGACCCGA AACACCTGAC TGCAAGCAAC
CACCTCCACA GGAGGTGGTT TTACCATGAA CTTCCTGTGT ACTGACTTGT GTTCATAATA
ATATTTTTGT GTTTAAACTC AATAAAGTCA CAAAAATGAT TGTAATCATG CAATGTAGTA
AAATTAAAAT ATTTGACCCT GTACACGATT CTGTGTAAAT GCCTTTTCTC AGAAGTGACC
GTCCAGGCGG TCACCGAACT CGATAATAAA GCGGCTCATT GCCATACGCC AGTCCGCAG
TGGCATCGTC CATTTCTGTG AAGCCGCCTG GATTGCCAGC CACACGACCT TTTTCACTGA
GTCATCCGTC GGGAACACCT TGCGTTTTTT GATGGCATGC CGGATTACGC TG*TTCAGCGA
CTCGATGGCG TTGGTTGTGT AGATGAC*
```

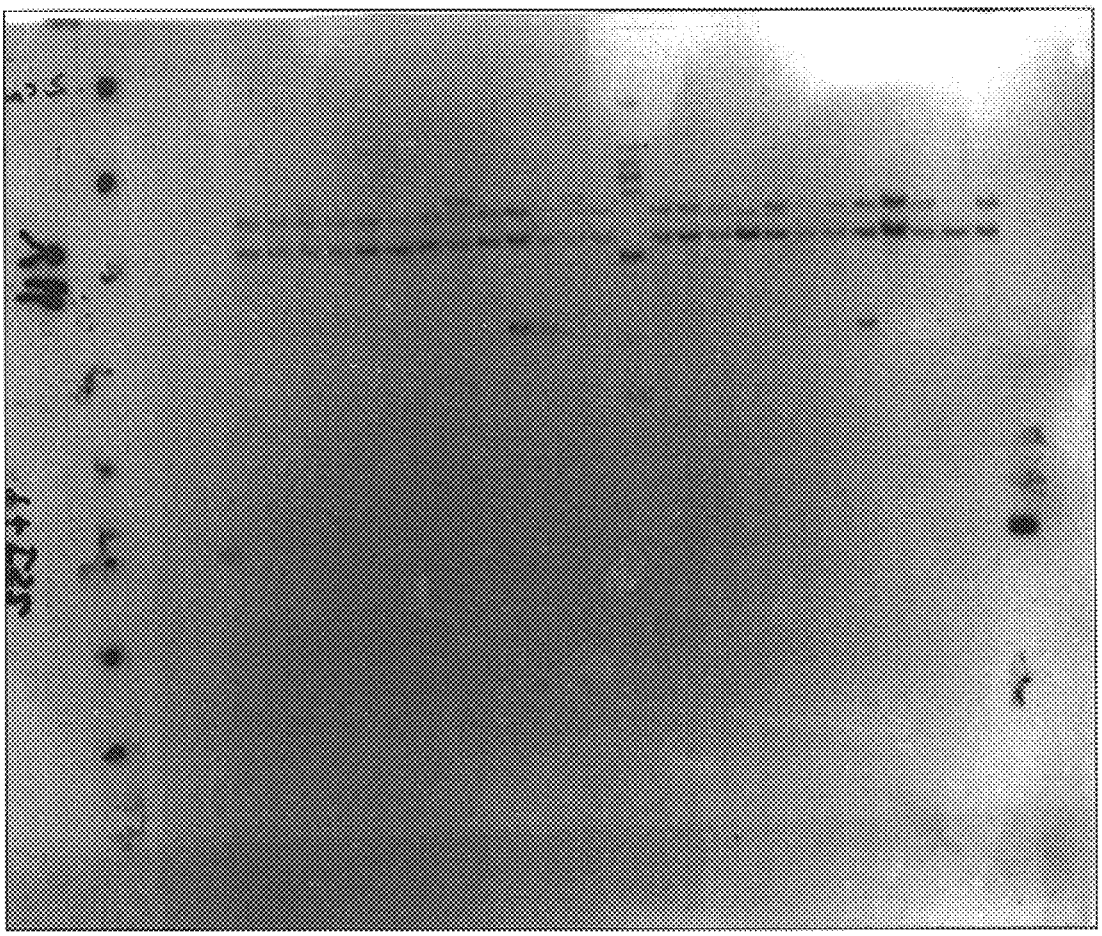

SEQUENCE LISTING

<160> NUMBER OF SEQ ID NOS: 16

<210> SEQ ID NO 1
<211> LENGTH: 441
<212> TYPE: DNA
<213> ORGANISM: E. coli

<400> SEQUENCE: 1

```
gcttcgatat tcagcccctg atgttcgcct ttctgcacct ggctcttttg cccataagat      60
taattttcct gttgaaacgc cctgttttca gattaaacag acggaactga aggggggctga    120 tgcgttacca cactggctgc ctttacaaaa aatcgccaac ggggcggtcg ggcattgcct    180
gggggcgaaa ggaattaatc tgctgatgag tacattgcag aaccgtctgg tcgatcatgg    240
ttatgtcacc acccgtgttc tggcaccttc gcaggattta aaaagcggta tcctccggct    300
ggttattatt cccggtgttg tgcgacatgt gcgtctgaca ccggacagtg atgactatat    360
tcagttgtat tcctcattcc cggcacacga aggttctctg ctggatttac gggacattga    420 gcagggggctg aatatcgaag c                                              441
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2

```
gcttcgatat tcagcccctg                                                  20
```

<210> SEQ ID NO 3
<211> LENGTH: 1331
<212> TYPE: DNA
<213> ORGANISM: E. coli

<400> SEQUENCE: 3

```
tagactggcc ccctgaatct ccagacaacc agtatcactt aaataagtga tagtcttaat      60
actagttttt agactagtca ttggagaaca gatgattgat gtcttagggc cggagaaacg    120
cagacggcgt accacacagg aaaagatcgc aattgttcag cagagctttg aaccggggat    180
```

```
gacggtctcc ctcgttgccc ggcaacatgg tgtagcagcc agccagttat ttctctggcg    240
taagcaatac taggaaggaa gtcttactgc tgtcgccgcc ggagaacagg ttgttcctgc    300
ctctgaactt gctgccgcca tgaagcagat taaagaactc cagcgcctgc tcggcaagaa    360
aacgatggaa aatgaactcc tcaaagaagc cgttgaatat ggacgggcaa aaaagtggat    420
agcgcacgcg cccttattgc ccgggatgg ggagtaagct tagtcagccg ttgtctccgg     480
gtgtcgcgtg cgcagttgta cgtcattctc agacgaaccg atgactggat ggatggccgc    540
cgcagtcgtc acactgatga tacgatgtg cttctccgta tacaccatgt tatcggagag     600
ctgcccacgt atggttatcg tcgggtatgg gcgctgcttc gcagacaggc agaacttgat    660
ggtatgcctg cgatcaatgc caaacgtgtt taccggatca tgcgccagaa tgcgctgttg    720
cttgagcgaa aacctactgt accgccatcg aaacgggcac atacaggcag agtggccgtg    780
aaagaaagca atcagcgatg gtgctctgac gggttcgagt tctgctgtga taacggagag    840
agactgcgtg tcacgttcgc gctggactgc tgtgatcgtg aggcactgca ctgggcggtg    900
actaccggcg gcttcaacag tcaaacagta caggacgtca tgctgggagc ggtggaacgc    960
cgcttcggca acgatcttcc gtcgtctcca gtggagtggc tgacggataa tggttcatgc    1020
taccgggcta atgaaacacg ccagttcgcc cggatgttgg gactggaacc gaagaacacg    1080
gcggtgcgga gtccggagag taacggaata gcagagaact tcgtgaaaac gataaagcgt    1140
gactacatca gtatcatgcc caaaccgac gggttaacgg cagcaaagaa ccttgcagag     1200
gcgttcgagc attataacga atggcatccg catagtgcgc tgggttatcg ctcgccacgg    1260
gaatatctgc ggcagcgggc ttgtaatggg ttaagtgata acagatgtct ggaaatatag    1320
gggcaaatcc a                                                        1331
```

<210> SEQ ID NO 4
<211> LENGTH: 535
<212> TYPE: DNA
<213> ORGANISM: E. coli
<220> FEATURE:
<221> NAME/KEY: unsure
<222> LOCATION: 1-535
<223> OTHER INFORMATION: "n" bases throughout the sequence may be A, T, C, G, other or unknown

<400> SEQUENCE: 4

```
gatggattta tcgtaataaa gacaacagcc aaataatgaa aaacataaaa ttttatctgc     60
atggcaaaga gataccagca gaaagaatat tagatacacc agagtggaaa gactaccgtc    120
caaaatactc cggttccaca tataaatatt cttaatgata gcaaaaaata tattttcgat    180
ataatcaatg ttatgattaa agagtatttc atcagggcag gtaaaaacag agtaaatcag    240
caaaagaagc tgatcttcag cgatactgac actaactgac ggtttaagcg gtcgtatgaa    300
gcagcagctt tccgacggac tgccatgcgg atcgtttacc ttttgggcta ttccgcccgt    360
catcaagcgg ctcacgagta ctgagtttat cagggatgat attgctgaca atgggtaatt    420
cgttgaaccg atgtgtactt tcactacata tcggtcaaca ccggtactgg ccgtgcaaca    480
tctcccagat gttacatccg tttttaccccn aaggaggcgg gacatanaat gttaa       535
```

<210> SEQ ID NO 5
<211> LENGTH: 2363
<212> TYPE: DNA
<213> ORGANISM: E. coli
<220> FEATURE:
<221> NAME/KEY: unsure
<222> LOCATION: 1-2363
<223> OTHER INFORMATION: "n" bases throughout the sequence may be
 A, T, C, G, other or unknown

<400> SEQUENCE: 5

```
aaccaacaat ggtataaaaa tgggccattc ttaatccatg caggacggaa tgggaggaag      60
tattcgccaa aagttaaatt caacagtctg ttggttttga gatataactn tcttttctaa     120
tatggacacc ttggctttgc tggttgttaa aattagcttg ttgattagta gtatggatag     180
aacttactct gttatttatt tctaaaaatg gaatttatca atgcttccta catcgcaatt     240
acgaccgacc gggacattct gctcctattc cgctgaaaca tcagcagaca tcaaaagcga     300
aatcacacca attcagatag aagaagcgcg ggccagtggt cgtttatata tcaaagattg     360
tgatattgag tatctgccac agttaccaaa cgaaataaca tcagttacaa tcgaaaactg     420
caacaacctg acaaccctta caggattgcc ggttaataca caaaacctct ccgtcattaa     480
ctgtgaaaaa ttacaaatca cagacatgcc atcaaccgta aaaaatntac atattgaatt     540
aactgattca ccatttatac atttcatatc tgaaggcatc gagtgcctga cggtttgcca     600
ctgctatata tctggagtgc cagagagtgt ccgctacctt gaaataaaag gtagcgccac     660
agacagcata aaaatgttcc aaacgggtta tcatctntca gcatcaatag ctataacccg     720
gagaatcagg ccagaattga ccacctgata tcaccgtcac tgaagacgct atcgctgact     780
ggatgtagca atattatact gccggagaaa cttccggaga gtgtgacatc ggtaaccatt     840
catgcggagc agaaaaccac gtggaacatc ggtgttgaag ggatgcctga tgggctggat     900
cttgatttac aaaatgtact actctctcca gatgtagtta aagcaaaaaa catcaccttt     960
cagggcaacg ctctggatgt ggccttacac tttcgcgagg gagacattgt ctatggacta    1020
tcttcaccca gagaaaaact tgtcaacagc attaaactag ttaacgactt ttccaaaaaa    1080
gatattataa ctcagaatac gttaacaaac gcagtatggg accccagaac acctcgcaaa    1140
tataagcaag atccacttat caaagagcca ttaaatgaac acgaaagagg aataaaattt    1200
aaacaacact taaggaatca caataattat aatgttacca tggccgacct ttccgtatac    1260
aatcgcgaca aattatgggc aaaaacaagc aaggccggcc tagagtttca gacattaaca    1320
cgcaataaaa cggttatttt ttgtgcggat gagcttgtca actcactcaa actcatagct    1380
aacaagtcag agggctatgg ccagagtatt accgccagcg aatttcgatg gatttaccgt    1440
aataaagaca acagccaaat aatgaaaaac ataaaatttt atctacatgg caaagagata    1500
ccagcagaaa gaatattaga tacaccagaa tggaaagact atcgtccaaa atactctggt    1560
tccacatata aatattctta atgataccaa cttataacgg aatagcataa aaacactttt    1620
catggagcaa aggagaaaac aatgccattt tcaatcaaaa acagatttc aagttcacaa     1680
gtacattacc cggaaatatc cggtcccata aaagacaagc cagcgtcaaa gaactgcata    1740
cttacatcaa caacatgtaa tgtagatagc tatacagtgt accaaaaaaa agcctgtagt    1800
tttgacatgc gcccacccgg cgcaggagaa agaaccccaa aactaaaact ctcagttact    1860
gagatgacat ggctatctaa aactatagaa acagagatac acaacacaaa agaatagcaa    1920
ccacttacca gagaacacaa aaagccacag acccgaaaca cctgactgca agcaaccacc    1980
tccacaggag gtggttttac catgaacttc ctgtgtactg acttgtgttc ataataatat    2040
ttttgtgttt aaactcaata aagtcacaaa atgattgta atcatgcaat gtagtaaaat     2100
taaatatttt gaccctgtac acgattctgt gtaaatgcct tttctcagaa gtgaccgtcc    2160
aggcggtcac cgaactcgat aataaagcgg ctcattgcca tacgccagtc ccgcagtggc    2220
```

```
atcgtccatt tctgtgaagc cgcctggatt gccagccaca cgacctttt cactgagtca      2280 tccgtcggga acaccttgcg ttttttgatg gcatgccgga ttacgctgtt cagcgactcg      2340
atggcgttgg ttgtgtagat gac                                              2363

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 6
tttcattatt tggctgttgt ct                                               22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 7
tttgatggca tgccggatta c                                                21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
ccaccttatg agtcagaata cg                                               22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 9
ggttctgcaa tgtactcatc ag                                               22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
ggtcgatcat ggttatgtca c                                                21

<210> SEQ ID NO 11
<211> LENGTH: 421
<212> TYPE: DNA
<213> ORGANISM: E. coli
<220> FEATURE:
<221> NAME/KEY: unsure
<222> LOCATION: 1-421
<223> OTHER INFORMATION: "n" bases throughout the sequence may be
      A, T, C, G, other or unknown

<400> SEQUENCE: 11
```

```
acaaaattgg ccgccccaat gggagttcaa aattggcccc ggaacttttc cagaacccat      60
acgaagtgct gggttgacgg acctcggggg aaaaaaggng tattaaaagt catcgaagca     120
tacgtctttg tcagggagtt tagtttccag gattcccggg gcggttcatg atgattgttg     180
gtatgacatg aataaaaggt ttttcgttag actggaaaat tatgttgcag gaacgagagg     240
actgaggaac aaagcttatt ccggcgctgt ccgtccttgc tgtcacngac acagatgtct     300
gctttattat cgcctttatc tcttcaggca gcggatgtcc ggcgtagcgg agatgaagca     360
tttatcattc agcagcagcg tcaggaagcc cttgagcaac aactgacgcc ttcagcccct     420
g                                                                    421
```

<210> SEQ ID NO 12
<211> LENGTH: 440
<212> TYPE: DNA
<213> ORGANISM: E. coli
<220> FEATURE:
<221> NAME/KEY: unsure
<222> LOCATION: 1-440
<223> OTHER INFORMATION: "n" bases throughout the sequence may be
      A, T, C, G, other or unknown

<400> SEQUENCE: 12

```
acagggctg gatttaggta acagccggat acagggtaca acatactgag ctgaatgcaa      60
ccagtggaaa tctgtctaca cagaatgcgc aactgagtgc cgatacgctt tccgcccgga    120
ctgccgggca gttcagcagt aatggcgta cgataaatgc cgacacactg cagatatcgg     180
cacaaagcct gtcaaatcgt aaaggcagtc tgattcagac gggaacaggg gattttcgc    240
tgagtctgcc gggaagcgtg gataaccggg aagggctgct tgcggccaat ggcgcggtgc    300
gtctggatgc actgagcctt gataatcgca aggggaaagt gcatgcggaa catttcaccc    360
ctcccttcag aaatctcccg ncccacgttt tctgaaaacc gtttgtggct ggtgtttgtg    420
ccggcattgc tggccgtcaa                                                440
```

<210> SEQ ID NO 13
<211> LENGTH: 1260
<212> TYPE: DNA
<213> ORGANISM: E. coli
<220> FEATURE:
<221> NAME/KEY: unsure
<222> LOCATION: 1-1260
<223> OTHER INFORMATION: "n" bases throughout the sequence may be
      A, T, C, G, other or unknown

<400> SEQUENCE: 13

```
acaaaattgg ccgccccaat gggagttcaa aattggcccc ggaacttttc cagaacccat      60
acgaagtgct gggttgacgg acctcggggg aaaaaaggng tattaaaagt catcgaagca    120
tacgtctttg tcagggagtt tagtttccag gattcccggg gcggttcatg atgattgttg    180
gtatgacatg aataaaaggt ttttcgttag actggaaaat tatgttgcag gaacgagagg    240
actgaggaac aaagcttatt ccggcgctgt ccgtccttgc tgtcacngac acagatgtct    300
gctttattat cgcctttatc tcttcaggca gcggatgtcc ggcgtagcgg agatgaagca    360
tttatcattc agcagcagcg tcaggaagcc cttgagcaac aactgacgcc ttcagcccct    420
gatgttcgcc tttctgcacc tggctctttt gcccataaga ttaattttcc tgttgaaacg    480
ccctgttttc agattaaaca gacggaactg aaggggctg atgcgttacc acactggctg    540
cctttacaaa aaatcgccaa cggggcggtc gggcattgcc tggggcgaa aggaattaat    600
```

```
ctgctgatga gtacattgca gaaccgtctg gtcgatcatg gttatgtcac cacccgtgtt      660
ctggcacctt cgcaggattt aaaaagcggt atcctccggc tggttattat tcccggtgtt      720
gtgcgacatg tgcgtctgac accggacagt gatgactata ttcagttgta ttcctcattc      780
ccggcacacg aaggttctct gctggattta cgggacattg agcaggggct ggatttaggt      840
aacagccgga tacagggtac aacatactga gctgaatgca accagtggaa atctgtctac      900
acagaatgcg caactgagtg ccgatacgct ttccgcccgg actgccgggc agttcagcag      960
taatggcggt acgataaatg ccgacacact gcagatatcg gcacaaagcc tgtcaaatcg     1020
taaaggcagt ctgattcaga cgggaacagg ggattttcg ctgagtctgc cgggaagcgt      1080
ggataaccgg gaagggctgc ttgcggccaa tggcgcggtg cgtctggatg cactgagcct     1140
tgataatcgc aagggggaaag tgcatgcgga acatttcacc cctccttca gaaatctccc     1200 gncccacgtt ttctgaaaac cgtttgtggc tggtgtttgt gccggcattg ctggccgtca     1260
```

```
<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 14
ggacagtgat gactatattc ag                                                22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 15
gcgtttcaac aggaaaatta atc                                               23

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: primer
<221> NAME/KEY: unsure
<222> LOCATION: 1-10
<223> OTHER INFORMATION: "n" is any nucleotide

<400> SEQUENCE: 16 ncagccctg                                                               10
```

NUCLEIC ACID SEQUENCES DIAGNOSTIC FOR PATHOGENIC *E.COLI* O157:H7, METHODS OF IDENTIFICATION AND KIT THEREFORE

FIELD OF THE INVENTION

This invention pertains to the fields of microbiology and biotechnology, and particularly to the field of identification of a particular nucleotide sequence which is diagnostic for the presence of a particular microorganism.

BACKGROUND OF THE INVENTION

*Escherichia coli* is a normal inhabitant of the lower gastrointestinal tract of animals, including humans, and is commonly found in fecal matter and raw sewage. Contamination of food with *E. coli*, often due to unsanitary conditions, can result in food poisoning, with clinical signs ranging from mild nausea and diarrhea, to severe illness and even death.

Fortunately, food poisoning with most strains of *E. coli* causes only mild illness. However, in recent years, a number of deaths have occurred in the United States and elsewhere due to outbreaks of illness following ingestion with food bearing *E. coli* bacteria. The causative organism of several of these outbreaks has been identified as a particular pathogenic strain of *E. coli* known

*E. coli* O157:H7, unlike ordinary commensal *E. coli* is an enterohemorrhagic bacterium and causes enterohemorrhagic colitis, hemolytic uremic syndrome, and mesenteric adenitis. The O157:H7 serotype is the most frequent enterohemorrhagic *E. coli*, and the most common cause of these life threatening illnesses.

*E. coli* O157:H7 infections can arise from a variety of sources but most commonly by the ingestion of contaminated foods or beverages. These foods, most commonly meat and dairy products, but also vegetables and fruits, such as berries, which are contaminated with *E. coli* O157:H7 are indistinguishable on visual or other sensory inspection from food which is not contaminated or which is contaminated with other strains of *E. coli*. Present methods for identifying *E. coli* O157:H7 are time consuming, expensive, and nonspecific. Thus, these methods are not optimal for routine testing of food for the detection of the O157:H7 strain.

One such currently available method involves a multi-day test whereby a suspected fecal or food sample is placed in an enrichment medium to select for gram negative bacteria. The sample is then incubated on filter paper on which colonies of *E. coli* O157:H7 will grow and produce toxins called verotoxins. The toxins are trapped in the filter paper and are identified using antibodies which specifically bind to the verotoxins.

Another method, disclosed in U.S. Pat. No. 5,354,661 (1994), utilizes a monoclonal antibody in an ELISA test to detect serotype O157:H7 in a sample. This method, however, has several disadvantages. For one thing, a presumptive diagnosis of serotype O157:H7 is obtained after about 20 hours, with a definitive diagnosis within an additional two days. Second, the antibody of the '661 patent is not specific for serotype O157:H7, but rather detects one other *E. coli* serotype, thereby possibly resulting in false positive tests.

U.S. Patent No. 5,475,098 (1995) discloses the detection of enterohemorrhagic *E. coli*, including serotype O157:H7, by the presence of a signature DNA sequence which is common to the group. False positive results are associated with this method as enterohemorrhagic *E. coli* other than O157:H7 are detected.

A serious need exists for a method of detection of O157:H7 which is inexpensive, rapid, and specific for this serotype. It is only by such a method that the risk of disease due to foods contaminated with O157:H7, or that serotype O157:H7 itself, can ever be eliminated.

SUMMARY OF THE INVENTION

This invention relates to diagnostic tests that will specifically identify *E. coli* O157:H7. In one embodiment the invention is an isolated DNA molecule comprising all or a portion of the DNA sequence shown in SEQ ID NO:1 and SEQ ID NO:13. The term "portion", as used in this specification and as it relates to SEQ ID NO:1 or SEQ ID NO:13, means a subset of contiguous bases of SEQ ID NO:1 or SEQ ID NO:13 which, when identified, is diagnostic of the presence of the entire sequence. In accordance with the present invention, a DNA sequence consecutively comprising 12 or more contiguous bases of SEQ ID NO:1 or SEQ ID NO:13 is considered to be a suitable "portion".

The isolated DNA molecule is pathognomic of *E. coli* serotype O157:H7. That is, the DNA molecule is diagnostic of the O157:H7 serotype and is not found in strains other than O157:H7.

The presence of a DNA molecule represented by the DNA sequence of SEQ ID NO:1 or SEQ ID NO:13 is useful for the definitive diagnosis of serotype O157:H7 in a fecal or food sample, or a crude microbiological sample from any source. Typically, the presence of a portion of the DNA sequence of SEQ ID NO:1 or SEQ ID NO:13 provides a presumptive diagnosis of O157:H7 although, because of the virtual certainty that the portion is part of the DNA sequence of SEQ ID NO:1 or SEQ ID NO:13, the detection of the portion, as defined above, may be considered a definitive diagnosis of the serotype.

A second embodiment of the invention is a method for the identification and diagnosis of *E. coli* O157:H7 in a sample using polymerase chain reaction (PCR). In accordance with the method of the invention, the *E. coli* strain is diagnosed by obtaining a sample suspected of harboring *E. coli* O157:H7, and determining by PCR, the presence or absence in the sample of a DNA molecule having a nucleotide sequence comprising the sequence shown in SEQ ID NO:1 or SEQ ID NO:13, which DNA molecule consecutively comprises 12 or more contiguous bases of SEQ ID NO:1 or SEQ ID NO:13, in addition to the oligonucleotide primers used for the amplification reaction. In a preferred embodiment, the PCR amplification is carried out using a single oligonucleotide primer, N58, (SEQ ID NO:2) to produce a DNA molecule having a nucleotide sequence comprising SEQ ID NO:1, or a portion thereof.

A third embodiment of the invention is a method for the identification and diagnosis of *E. coli* O157:H7 in a sample by identifying by Southern blotting a restriction fragment comprising the sequence shown in SEQ ID NO: 1 or SEQ ID NO:13 or a portion thereof. The restriction fragment comprising SEQ ID NO:1 or SEQ ID NO:13 or portion is identified by digesting DNA from a sample suspected of harboring *E. coli* O157:H7 with an appropriate restriction enzyme, followed by the detection of said restriction fragment by hybridizing the digested DNA sample with a probe that anneals to SEQ ID NO:1 or SEQ ID NO:13 or a portion thereof.

A fourth embodiment of the invention is a method for the identification and diagnosis of *E. coli* O157:H7 in a sample by identifying by Southern blotting a restriction fragment comprising the IS2 insertion element represented by SEQ ID NO:3 and which also comprise the nucleotide sequences represented by SEQ ID NO:4 and SEQ ID NO:5, or a portion thereof, such restriction fragment being diagnostic of *E. coli* O157:H7. Unexpectedly, it has been discovered that the IS2 insertion element stably resides in a portion of the genome that is unique to, and therefore diagnostic of *E. coli* O157:H7. In this embodiment of the invention, restriction fragments comprising this unique nucleotide region of *E. coli* O157:H7 which comprise the IS2 insertion element are identified by Southern blotting and are detected by hybridization using the IS2 nucleotide sequence, or a portion thereof as a probe. In a preferred embodiment if the invention, the restriction enzymes EcoRI or EcoRV are used to digest the DNA of a sample suspected of harboring *E. coli* O157:H7, which generate diagnostic restriction fragments of about 8.5 kbp and about 10 kbp, respectively.

A fifth embodiment of the invention is a method for the identification and diagnosis of *E. coli* O157:H7 in a sample by PCR. In this embodiment, the PCR reaction is carried out with oligonucleotide primers that anneal to the nucleotide sequences which are unique to *E. coli* O157:H7 and which comprise SEQ ID NO:4 and SEQ ID NO:5. These primers therefore anneal to nucleotide sequences that flank the 5' and 3' ends of the IS2 insertion element, and generate an amplification product that is diagnostic of *E. coli* O157:H7. In a preferred embodiment, the oligonucleotide primers of the invention are represented by SEQ ID. NO:6 and SEQ ID NO:7 and amplify a 1.4 kbp amplification product which is diagnostic of *E. coli* O157:H7. Diagnostic tests that utilize an outwardly directed primer that anneals within the IS2 sequence (SEQ ID NO:3) and an inwardly directed primer that anneals to the sequences which flank on the right or left sides of the IS2 sequence (SEQ ID NO:4 or SEQ ID NO:5, respectively) are also considered to be within the scope of the invention. For example, a primer pair comprising SEQ ID NO:6 and a primer that anneals to the IS2 sequence (SEQ ID NO:3) can be used for generating a fragment comprising the right end of the IS2 sequence (SEQ ID NO:3) and at least a portion of the right flanking sequence, and the primer pair comprising SEQ ID No. 7 and a primer that anneals to the IS2 sequence (SEQ ID NO:3) can be used for generating a fragment comprising the left end of the IS2 sequence (SEQ ID NO:3) and at least a portion of the left flanking sequence.

A sixth embodiment of the invention is a method for the identification and diagnosis of *E. coli* O157:H7 in a sample using sequentially, or together, the diagnostic tests of the second, third, fourth and fifth embodiments of the invention.

A seventh embodiment of the invention are kits comprising the oligonucleotide primers, DNA fragments and necessary reagents to conduct the PCR and/or Southern blot diagnostic tests described above. The kit for the detection of SEQ ID NO:13 or a protion thereof by PCR comprises the primer represented by SEQ ID NO:2, positive and negative control templates comprised of genomic DNA from *E. coli* O157:H7 and *E. coli* K12, respectively, the isolated DNA fragment represented by SEQ ID NO:1 to serve as a size reference for the expected product generated by the SEQ ID. NO:2 primer, and a primer represented by SEQ ID NO:8, which when used in conjunction with SEQ ID NO:2, functions as an internal control to verify that the proper conditions for PCR amplification are used. Kits which contain primers other than SEQ ID. NO:2 that anneal to SEQ ID NO:13 are also considered to be within the scope of the invention.

A kit for the detection of DNA fragments comprising SEQ ID NO:13 by Southern blotting comprises the isolated DNA fragments represented by SEQ ID NO:1 and SEQ ID NO:13. These fragments function as hybridization probes to detect restriction fragments comprising SEQ ID NO:13 in genomic DNA from an appropriate sample. Genomic DNA from *E. coli* strains O157:H7 and K12 is included to serve as the positive and negative control, respectively.

A kit for the detection of the IS2 sequence (SEQ ID NO:3) and the diagnostic sequences that flank IS2 (SEQ ID NO:4 and SEQ ID NO:5) by PCR comprises matched pairs of primers represented by SEQ ID NO:6 and SEQ ID NO:7, SEQ ID NO:6 and a primer that anneals to the IS2 sequence (SEQ ID NO:3), and SEQ ID NO:7 and a primer that anneals to the IS2 sequence (SEQ ID NO:3), and positive and negative control DNAs comprising genomic DNA from *E. coli* strains O157:H7 and K12, respectively.

A kit for the detection of DNA fragments comprising SEQ ID NO:3, SEQ ID NO:4, SEQ ID NO:5 or portions of these sequences by Southern blotting comprises isolated DNA fragments represented by SEQ ID NO:3, SEQ ID NO:4 and SEQ ID NO:5 which serve as hybridization probes, and positive and negative control DNAs comprising genomic DNA from *E. coli* strains O157:H7 and K12, respectively.

An eighth embodiment of the invention is a method for amplifying a DNA molecule, comprising cyclically permitting a single primer of about 20 nucleotides to anneal to a DNA molecule at a temperature of between 42° C. and 52° C., and extending the primed DNA by a DNA polymerase at a temperature of between 68° C. and 72° C.

BRIEF DESCRIPTION OF THE FIGURES

FIG. 1 shows the nucleotide sequence of a 441 base pair amplicon (SEQ ID NO:1) which sequence is diagnostic of *E. coli* O157:H7. The first 9 bp and final 11 bp of the sequence are derived from the N58 primer (SEQ ID NO:2) and are not encoded by *E. coli* O157:H7 genomic DNA.

FIG. 2 shows the nucleotide sequence of the IS2 insertion element (SEQ ID NO:3); bold letters above indicate base substitutions found in the IS2 from *E. coli* O157:H7 as compared to the prototype IS2 sequence from *E. coli* K12.

FIG. 3 shows the nucleotide sequence of a 535 bp region (SEQ ID NO:4) downstream from the IS2 insertion element (SEQ ID NO:3), which sequence is unique to *E. coli* O157:H7.

FIG. 4 shows the nucleotide sequence of a 2363 bp region upstream from the IS2 insertion element, which sequence is unique to *E. coli* O157:H7 (SEQ ID NO:5). The IS2 sequence (SEQ ID NO:3) follows immediately downstream from this sequence.

DETAILED DESCRIPTION OF THE INVENTION

Figure 5:
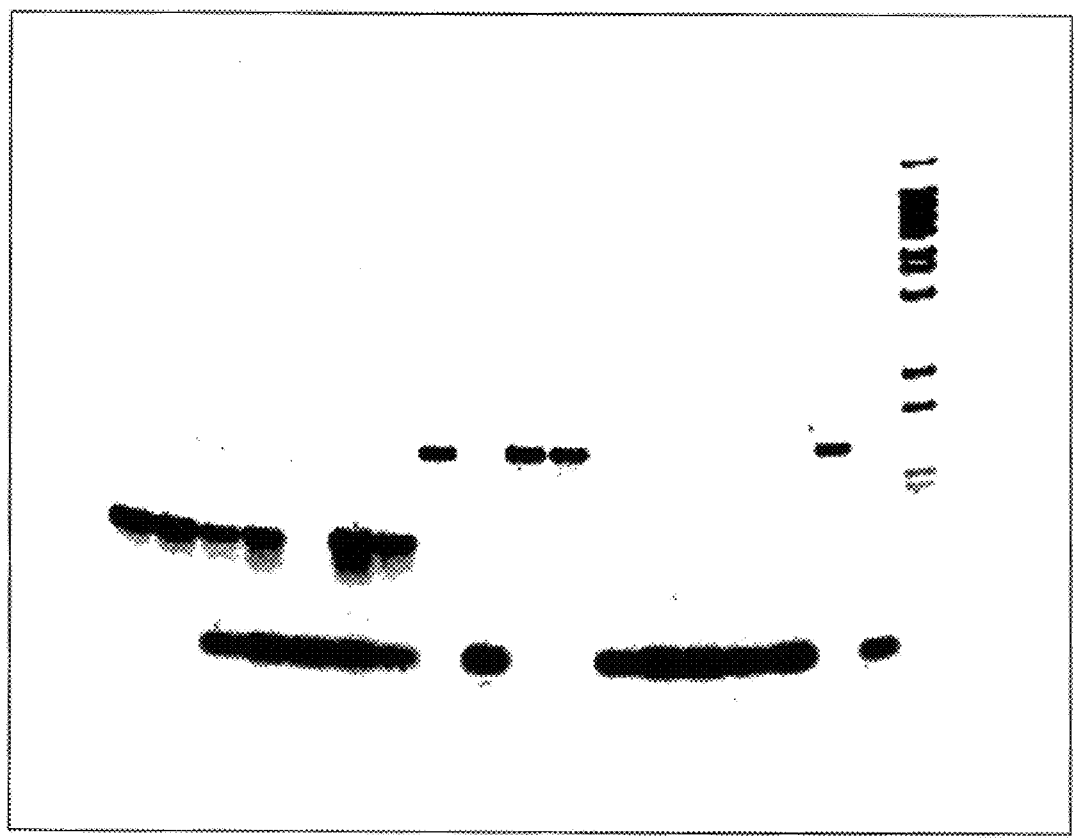
FIG. 5 compares the PCR products obtained from various *E. coli* strains using primer N58 (SEQ ID NO:2) alone with those obtained using both N57 (SEQ ID NO:8) and N58 (SEQ ID NO:2).

The first embodiment of the invention is an isolated or purified DNA molecule which comprises a sequence as shown in SEQ ID NO:1 or SEQ ID NO:13, or a portion thereof, the term "portion" being defined above. The nucleotide sequence of the DNA molecule of the invention has been discovered in accordance with the invention to exist in nearly every isolate of E. coli serotype O157:H7 which has been tested and not to exist in any isolates of E. coli other than serotype O157:H7. Moreover, searches of DNA databases has revealed that the DNA of the invention is unique.

Because the DNA sequence of SEQ ID NO:1 or SEQ ID NO:13 forms part of the genome of serotype O157:H7, and of no other known organism, the DNA sequence of the invention may be used to definitively diagnose the presence of E. coli O157:H7 in any sample, such as feces or food. In addition, the presence of any portion of the DNA molecule which is indicative of the presence of the entire sequence of the DNA molecule in a sample gives strong presumptive evidence of the presence of E. coli O157:H7 in the sample. Generally, the presence of a DNA sequence comprising 12 or more contiguous bases of the DNA sequence of the DNA molecule of the invention, as shown in SEQ ID NO:1 or SEQ ID NO:13, is likely to be diagnostic of the presence of the entire sequence, and therefore of the presence of E. coli O157:H7 in the sample. Thus, in this specification, reference to detection of the DNA molecule, or the DNA sequence of the DNA molecule, of the invention, includes detection of a portion of the molecule as defined herein.

In accordance with the invention, a method is provided for the identification or diagnosis of E. coli serotype O157:H7 in a sample, such as food, fecal, or other sample. In one embodiment, the method comprises digesting the DNA in the sample to be analyzed with a suitable restriction enzyme and rendering it accessible to an external nucleic acid probe, contacting DNA from the sample with a nucleic acid probe which anneals, typically under high stringency conditions, to the 441 bp DNA sequence shown in Seq. ID NO:1 or to SEQ ID NO:13, and detecting the probe bound to a sample DNA which comprises the nucleic acid sequence shown in Seq. ID NO:1 or SEQ ID NO:13, or a diagnostic portion thereof.

Virtually any restriction enzyme may be used for the Southern blotting analysis to detect restriction fragments comprising the sequences of SEQ ID NO:1 or SEQ ID NO:13. Preferably, although not necessarily, the restriction enzyme should not cut within the sequence of SEQ ID NO:1 or SEQ ID NO:13. However, if it is desired to diagnose the presence of serotype O157:H7 by detecting only a diagnostic portion of the sequence of SEQ ID NO:1 or SEQ ID NO:13, an endonuclease which cuts into the sequence may be satisfactory.

For instance, the restriction fragment comprising the DNA of SEQ ID NO:1 in an EcoRI digested DNA sample may be identified by hybridization with the 441 bp DNA sequence or a portion thereof. Detection of a digestion fragment of about 7.5 kb containing the 441 bp sequence of SEQ ID NO:1 is diagnostic of E. coli O157:H7. The diagnosis of serotype O157:H7 may also be made by identification of an about 1.5 kb EcoRV fragment containing the 441 bp sequence of SEQ ID NO:1.

In addition, because the Southern Analysis products are diagnostic of E. coli O157:H7, it is conceived that a portion of the O157:H7 genome flanking the 441 bp sequence shown in SEQ ID NO:1 is likewise diagnostic of serotype O157:H7. These diagnostic flanking regions, which are considered to be equivalent to SEQ ID NO:1 for purposes of the diagnostic method of the invention, may be identified readily by several known methods.

For example, the 441 bp amplicon, or a portion thereof, may be used as a primer to amplify a portion of the O157:H7 genome, which portion may be sequenced by known methods. Alternatively, the Southern blotting products may readily be sequenced to determine the sequence of the nucleotides which border the 441 bp diagnostic sequence. Indeed, these techniques have already been used to determine the sequences flanking the 441 bp fragment. These sequences are represented by SEQ ID NO:11 and SEQ ID NO:12 and a composite of the 441 bp sequence (SEQ ID NO:1) and the sequences that flank this fragment in the genome (SEQ ID NO:11 SEQ ID NO:12) is represented by SEQ ID NO:13.

The use of these flanking, or border sequences, or additional sequences that flank SEQ ID NO:13, to diagnose the presence of E. coli serotype O157:H7 is therefore considered to be within the scope of the method of the invention as disclosed herein.

The probe for the detection of restriction fragments comprising the 441 bp sequence may be any sequence which will anneal to the sequence represented by SEQ ID NO:1. Thus, the probe may anneal to a portion of the E. coli genome which includes SEQ ID NO:1 or to a portion of the genome which lies adjacent to the portion of the genome which includes SEQ ID NO:1.

In another embodiment of the invention, the diagnostic sequence represented by SEQ ID NO:1 or SEQ ID NO:13 is identified in a sample by PCR. In a preferred embodiment, the DNA from the sample is amplified, such as by the polymerase chain reaction.

Suitable primers for amplification of the DNA include those primers which will yield a DNA molecule comprising the nucleotide sequence of SEQ ID NO:1 or SEQ ID NO:13, or a diagnostic portion thereof. Generally, such primers are 10 to 30 bases in length and are selected to anneal to the E. coli genome so as to yield the DNA molecule.

If desired, the amplification may be performed as in standard PCR, as described in Ausubel et al., Current Protocols in Molecular Biology, John Wiley & Sons, Inc. (1994–1997), incorporated herein by reference. In this method, two primers are allowed to anneal to opposite strands of a sample DNA at an annealing temperature between 55° C. and 70° C. This is followed by extension of the DNA at a temperature of 72° C.

It has been discovered, however, in an improvement of the PCR method, that extraneous amplification products can often be reduced or eliminated by adjusting the PCR procedure to utilize a single primer and temperatures which are lower than those disclosed by Ausubel. It has been discovered that amplification of the DNA of a sample may be optimized by using a single primer, an annealing temperature of between about 42° C. to 52° C., and an extension temperature of less than 72° C., such as about 68° C. to 71° C.

In a preferred embodiment, the DNA from a sample to be analyzed is amplified using a single oligonucleotide primer, assigned the name N58, having the sequence: 5'-GCTTCGATATTCAGCCCCTG-3' (SEQ ID NO:2). It has also been discovered that the 3' sequence of N58 (SEQ ID NO:2) is important for the amplification of the 441 bp amplicon. Thus, other primers that differ in their 5' sequence but which match the 3' sequence of N58 (SEQ ID NO:2), i.e., primers with the sequence of 5'-(X)$_n$-CAGCCCCTG-3'

(SEQ ID NO:16), where X is any nucleotide and "n" is an integer, will be suitable for amplifying the 441 bp amplicon. Preferably, the annealing temperature is about 52° C. and the extension temperature is about 68° C.

The detection step of the method may be by any means by which the DNA sequence of SEQ ID NO:1 or SEQ ID NO:13, or diagnostic portion thereof, may be determined. For example, the detection may be visual, by identifying the amplicon of 441 bp having a sequence of SEQ ID NO:1 or SEQ ID NO:13 in agarose gels containing ethidium bromide.

As another example of a suitable detection step, the DNA sequence may be detected by hybridization using a probe that anneals to the 441 bp sequence of SEQ ID NO:1, or the sequence represented by SEQ ID NO:13, which comprises the 441 bp sequence of SEQ ID NO:1 and additional 5'- and 3'-flanking sequences, or a portion thereof.

In yet another embodiment of the invention, E. coli O157:H7 can be specifically identified by hybridization using a probe comprising sequences of the IS2 insertion element. Insertion elements are naturally occurring mobile genetic elements that are found in virtually all bacteria. It has been unexpectedly discovered that the IS2 insertion element stably resides in a region of the E. coli O157:H7 genome that is specific, or unique, to E. coli O157:H7 and is not found in other bacteria. In accordance with the invention, it has been discovered that restriction fragments comprising IS2, or portions of IS2 also comprise a portion of the chromosomal sequences which are unique to and diagnostic for E. coli O157:H7. These diagnostic restriction fragments are readily detected by hybridization using a probe that anneals to IS2 sequences.

For example, in a preferred embodiment of the invention, DNA from a sample suspected of containing E. coli O157:H7 is digested with EcoRI or EcoRV and the resulting collection of fragments is fractionated according to their size in an agarose gel. After transfer of the fragments to a suitable hybridization membrane, the fragments are allowed to anneal to a probe comprising the IS2 DNA sequence or a portion of the IS2 DNA sequence. After washing the filter to remove unbound probe, hybridizing fragments are detected. Under these conditions, it was discovered that E. coli O157:H7 possessed EcoRI and EcoRV restriction fragments of about 8.5 kbp and 10 kbp, respectively, which annealed to the IS2 probe and were not present in other E. coli strains or related bacteria. Nucleotide sequencing of the DNA regions flanking the 5' and 3' ends of the IS2 insertion element within these restriction fragments identified portions of the E. coli O157:H7 chromosome that are unique for this strain (represented by SEQ ID NO:4 and SEQ ID NO:5). The diagnostic test of the invention is not limited to ECORI and EcoRV restriction fragments. Virtually any restriction fragment, generated by any restriction enzyme, which comprises the IS2 sequence or a portion of the IS2 sequence, and also comprises a flanking sequence which is unique to E. coli O157:H7 are considered within the scope of the present invention.

In another preferred embodiment of the invention, oligonucleotide primers, represented by SEQ ID NO:6 and SEQ ID NO:7, which anneal to the unique 5' and 3' sequences (SEQ ID NO:4 and SEQ ID NO:5) which flank the IS2 insertion element were utilized to generate an amplicon of 1.4 kbp by PCR, which amplicon is specific for and diagnostic of E. coli O157:H7. Since these primers anneal to DNA that is present only in E. coli O157:H7, no amplicon is generated in PCR reactions with other strains of E. coli, even if these strains possess copies of the IS2 insertion element residing in other regions of their chromosomes. Diagnostic tests that utilize an outwardly directed primer that anneals within the IS2 sequence (SEQ ID NO:3) and an inwardly directed primer that anneals to the sequences which flank on the right or left sides of the IS2 sequence (SEQ ID NO:4 or SEQ ID NO:5, respectively) are also considered to be within the scope of the invention. For example, a primer pair comprising SEQ ID NO:6 and a primer that anneals to the IS2 sequence (SEQ ID NO:3) can be used for generating a fragment comprising the right end of the IS2 sequence (SEQ ID NO:3) and at least a portion of the right flanking sequence, and the primer pair comprising SEQ ID NO:7 and a primer that anneals to the IS2 sequence (SEQ ID NO:3) can be used for generating a fragment comprising the left end of the IS2 sequence (SEQ ID NO:3) and at least a portion of the left flanking sequence.

A kit for practicing the invention may comprise the DNA molecule of SEQ ID NO:1 or SEQ ID NO:13, or portion thereof, or primers which anneal to the DNA molecule or portion, for detection of E. coli serotype O157:H7. For example, a suitable kit for detection of serotype O157:H7 may comprise reagents for PCR amplification and detection of the DNA molecule of SEQ ID NO:1 or SEQ ID NO:13. Such a kit typically comprises samples of the oligonucleotide primers (a primer or a pair of primers), complementary to about 10 to 30 consecutive nucleotides of nucleotide sequence of SEQ ID NO:1, or of SEQ ID NO:3, SEQ ID NO:4, SEQ ID NO:5, or SEQ ID NO:13, which primers are used to amplify a DNA sequence of a sample, and a probe sequence for detection of the DNA sequence of the invention, or portion, in the amplified DNA sequence. The kit may further comprises instructions and reagents for amplification, such as the four dNTPs, DNA polymerase, and buffered salt solutions. Preferably, the kit comprises a positive control template of genomic DNA from E. coli serotype O157:H7 , a negative control template of genomic DNA from E. coli K12 and instructions for use of these reagents.

It is also possible to identify E. coli O157:H7 by techniques designed to detect the mRNA transcripts or the protein products produced from genes that reside within the diagnostic DNA regions represented by SEQ ID NO:4, SEQ ID NO:5 and SEQ ID NO:13. For example, the probes, or portions thereof, used for detecting restriction fragments comprising SEQ ID NO:1, SEQ ID NO:4, SEQ ID NO:5, or SEQ ID NO:13 will also hybridize in Northern blots with mRNA transcripts that are generated from open reading frames contained in these sequences. In addition, antibodies that are specific for proteins which are encoded within these diagnostic genomic DNA fragments are themselves likely to be diagnostic of E. coli O157:H7. Polyclonal or monoclonal antibodies that are specific for these peptides are made by immunizing animals with synthetic peptides derived from the amino acid sequences deduced from the DNA sequences shown in SEQ ID NO:1 SEQ ID NO:4, SEQ ID NO:5, and SEQ ID NO:13. Identification of E. coli O157:H7 in a sample is subsequently carried out using ELISA. Briefly, the crude sample is first reacted with the polyclonal or monoclonal antibodies described above. After appropriate incubation, unbound antibody is removed by washing with buffer and subsequently, bound antibody is reacted with an antibody conjugate which specifically reacts with the first antibody and which is covalently linked to a detectable label such as an enzyme, or a fluorescently or radioactively labeled compound. Bound label is then quantified by an appropriate method.

The various embodiments of the invention are illustrated by the following examples which are solely illustrative of the invention and are not meant to limit the scope of the invention.

EXAMPLE 1

PCR Analysis of *E. coli* Serotype O157:H7

Chromosomal DNA from *E. coli* serotype O157:H7 was isolated and amplified by PCR using a pair of primers, N57 (SEQ ID NO:8) and N58 (SEQ ID NO:2), designed to amplify the rpoS gene. The nucleotide sequences of these primers is 5'-CCACCTTATGAGTCAGAATACG-3' (SEQ ID No. 8), and 5'-GCTTCGATATTCAGCCCCTG-3' (SEQ ID No. 2), respectively. The amplified PCR products were isolated and elecrophoresed in an agarose gel. Unexpectedly, two amplicons were detected from many *E. coli* O157:H7 strains in these reactions (see FIG. 5). One amplicon was approximately 900 bp long and was consistent with the size of the expected product generated from the rpoS gene. The second amplicon was determined to have a sequence of 441 bp and was not similar to the rpoS gene sequence or to other sequences in the current sequence DataBases. The sequence of the 441 bp amplicon is shown in SEQ ID No:1 and in FIG. 1.

PCR amplification was then performed on the chromosomal DNA using only one of the above primers, the N58 primer (SEQ ID NO:2), as the sole PCR primer. Using the single primer, the 441 bp amplicon was again obtained, using an annealing temperature of 42° C. and an extension temperature of 68° C. The 900 bp amplicon was not produced.

In FIG. 5, lanes 1–10 were from amplification reactions using both N57 (SEQ ID NO:8) and N58 (SEQ ID NO:2) present; lanes 11–19 had only N58 (SEQ ID NO:2) in the reactions. Lane 1 reaction was a negative control using water in place of template DNA. The other reactions had DNA from the following strains: *E. coli* K12 isolates 4717 (2 & 11) and 4789 (3 & 12); *E. coli* O157:H7 isolates 8127 (4 & 13), 7329 (5 & 14), 8101 (6 & 15), 8102 (7 & 16), 8103 (8 & 17), 8424 (9 & 18), and 8436 (10 & 19). Lane 20 has size standards (a BstEII digest of λ phage DNA). The 0.9 kb amplicon is from the rpoS gene and requires both primers; the 0.4 kb amplicon is generated with a single primer, N58 (SEQ ID NO:2), and is characteristically produced only from *E.coli* O157:H7 bacterial DNA. All samples were electrophoresed in 1% agarose and fragments were visualized by ethidium bromide staining.

Subsequent characterization of the regions flanking the 441 bp amplicon in the *E. coli* O157:H7 genome (see Example 6 below) suggest that the 3' end of N58 (SEQ ID NO:2) is important for amplification of the 441 product. Thus, primers having a different 5' sequence from N58 but having the 3' sequence matching the N58 oligonucleotide (SEQ ID NO:2), i.e., 5'(X)$_n$-CAGCCCCTG-3' (SEQ ID NO:16), are also suitable for amplifying the 441 bp amplicon from O157:H7 strains.

EXAMPLE 2

Pcr Analysis of Multiple Isolates of Serotype O157:H7

PCR analysis was repeated on over 90 different isolates of *E. coli* serotype O157:H7, using the N58 primer (SEQ ID NO:2) as a single PCR primer. The 441 bp amplicon obtained in Example 1 was obtained from nearly all of the isolates, as summarized in Table 1.

From several of the isolates, an additional amplicon of about 200 bp was produced. This variable product was eliminated by adjusting the PCR conditions to use an annealing temperature of 52° C. and an extension temperature of 68° C.

EXAMPLE 3

PCR Analysis of Bacteria other than *E. Coli* O157:H7

PCR was performed, as in Example 2, on over 80 different isolates of *E. coli* strains other than O157:H7 and using other species of Escherichia and Shigella. As shown in Table 1, none of these bacteria yielded the 441 bp amplicon of Example 1.

EXAMPLE 4

Novelty of the Sequence of the 441 BP Amplicon

The 441 bp amplicon of Example 1, as shown in FIG. 1 and SEQ ID NO:1, was compared, using a BLASTN/nr search (Atschul, S .F., Madden, T. L., Schaffer, A. A., Zhang, J., Zhang, Z., Miller, W. and Lipman, D. J. 1997. Gapped BLAST and PSI-BLAST: A new generation of protein database search programs. Nuc Acids Res. 25:3389–3402), with DNA sequences in GenBank, EMBL, DBJ, and PDB databases. No matches and no significant homology were found with the DNA sequences of these databases.

The sequence of SEQ ID NO:1 was translated into possible amino acid sequences for all six reading frames and these putative amino acid sequences were compared to sequences in protein databases using a BLASTX/nr search (Atschul, S. F., Madden, T. L., Schaffer, A. A., Zhang, J., Zhang, Z., Miller, W. and Lipman, D. J. 1997. Gapped BLAST and PSI-BLAST: A new generation of protein database search programs). Nuc Acids Res. 25:3389–3402). Only one highly homologous protein sequence was discovered, that of the HecB protein of the plant pathogen *Erwinia chrysanthemi*.

The HecB protein has 17 identical and 10 conservative substitutions over a 52 amino acid stretch, and 9 identical and 13 conservative substitutions over a second 28 amino acid stretch of comparison to one of the possible amino acid sequences encoded by the sequence of SEQ ID NO:1. An additional protein, the HlyB (hemolysis activator protein precursor), recognized as homologous to HecB and other proteins which form Type III protein secretion apparati of plant and animal pathogens, is less significantly related to the novel sequence of SEQ ID NO:1. All BLAST searches were carried out at http://www.ncbi.nlm.nih.gov, and utilized the default search parameters.

EXAMPLE 5

Southern Analysis

Figure 6A:
FIG. 6A shows a Southern blot of genomic DNA derived from various *E. coli* strains using the 0.4 kbp fragment (SEQ ID NO:1) as a probe.

Southern analysis was performed by digesting genomic DNA from several isolates of *E. coli* O157:H7 with the restriction enzyme EcoRI and separating the digestion fragments by gel electrophoresis. The 441 bp amplicon (SEQ ID NO:1) was found to anneal to a digestion fragment of approximately 7.5 kb (see FIG. 6A). In FIG. 6, lane 1 represents a DNA standard (λ.gal-IS2 DNA digested with HindIII), lanes 2 and 19: also a DNA standard (λ.gal-IS2 DNA partially digested with HincII), lanes 3 and 4: *E. coli* O157:H7 isolates 8127 and 8185 (cured of pO157 plasmid), lanes 5 through 10: various serotypes of *E. coli*—strains 8471, 8472, 8473, 8474, 8475, 8476, lanes 11 through 13 and 18: *E. coli* K12 strains 4716 derivative, 0489, 0489 derivative, and 4716, lanes 14 through 17: *E. coli* C strains, derivatives of 0889 with an IS2 transduced from *E. coli* K12.

Southern analysis was also performed using EcoRV as described above. The 441 bp amplicon (SEQ ID NO:1) was found to anneal to a digestion fragment of approximately 1.5 kb (not shown).

Both the 7.5 kb EcoRI and the 1.5 kb EcoRV digestion fragments were obtained on Southern analysis of over 30 different isolates of *E. coli* O157:H7. Neither of these digestion fragments were obtained on Southern analysis of any bacterial strain other than *E. coli* serotype O157:H7 (see Table 1).

EXAMPLE 6

Amplification and Detection of DNA Flanking The Sequence of Sequence ID NO. 1

The sequence of the unique internal region of the 0.4 kb amplicon (SEQ ID NO:1) permits the design of outward directed primers to amplify the DNA flanking the region of the *E. coli* O157:H7 chromosome containing this sequence. These sequences are also likely to be diagnostic of *E. coli* O157:H7. This is accomplished by inverse PCR (IPCR).

The chromosomal DNA of serotype O157:H7 is digested with EcoRI, or any other restriction enzyme which cuts the chromosomal DNA on both sides of SEQ ID NO:1 and does not recognize a restriction site within SEQ ID NO:1. The digest is ligated at dilute DNA concentration to obtain circularized DNA fragments joined at the restriction sites. The circularized DNA contain the sequence of SEQ ID NO:1 plus DNA from both 3' and 5' to SEQ ID NO:1.

The circularized DNA is used as a template for IPCR using primers N172 (SEQ ID NO:14) and N173 (SEQ ID NO:15), which are designed to pair with SEQ ID NO:1 and to extend outward into the regions 3' and 5' to SEQ ID NO:1. The nucleotide sequences of N172 and N173 are 5'-GGACAGTGATGACTATATTCAG-3' (SEQ ID NO:14) and 5'-GCGTTTCAACAGGAAAATTAATC-3'(SEQ ID NO:15), respectively. Because the restriction fragment is circularized, the primers are directed towards each other and produced an amplicon of about 7 kbp, consistent with the size of the product predicted from the EcoRI restriction fragment itself. The IPCR amplicon, which anneals to a DNA probe comprising the sequence of SEQ ID NO:1, was isolated by gel electrophoresis and visualized after staining with ethidium bromide.

EXAMPLE 7

Sequencing of DNA Flanking the Sequence of SEQ ID NO. 1

The isolated IPCR amplicon DNA of Example 6 is directly sequenced to determine the sequences flanking the 3' and 5' ends of the 441 bp sequence by using the N75 (SEQ ID NO:9) and N76 (SEQ ID NO:10) pair of nested primers which anneal to the 441 bp sequence at positions closer to the 3' and 5' ends of the sequence than the primers used in Example 6 and which primers are extended outward from the sequence. The nucleotide sequences of N75 and N76 are 5'-GGTTCTGCAATGTACTCATCAG-3' (SEQ ID NO:9) and 5'-GGTCGATCATGGTTATGTCAC-3' (SEQ ID NO:10), respectively.

Alternatively, the gel isolated IPCR amplicon is cloned into a plasmid vector by opening the circularized amplicon with a restriction enzyme, blunt-ending the amplicon with T4 DNA polymerase, and ligating to a blunt-cut plasmid vector, such as EcoRV digested pBSIISK(+). The ligated plasmid-amplicon is transformed into an XL1-Blue non-pathogenic *E. coli* strain (Stratagene). Transformants are selected on medium containing ampicillin.

Sequencing is then accomplished with the dideoxy termination method using two sets of primers that anneal within the 441 bp region or within the Bluescript vector. Thus nucleotide sequence is determined outwardly from the 441 bp sequence which resides within the cloned fragment, and inwardly (i.e. into the insert from the Bluescript vector) from the pUC-forward and pUC-reverse primers, which anneal to vector sequences. If necessary, additional primers are synthesized to anneal to portions of the nucleotide sequence determined by the original primer sets, described above. This is repeated until both strands of the cloned DNA are sequenced in their entirety. The sequences represented by SEQ ID NO:11 and SEQ ID NO:12 were determined by these methods. These sequences comprise the nucleotide sequences which flank the 441 bp amplicon (SEQ ID NO:1) in the *E. coli* O157:H7 genome. SEQ ID NO:13 represents a composite of SEQ ID NO:1, SEQ. ID NO:11, and SEQ. ID NO:12.

EXAMPLE 8

Southern Blots and IPCR of *E. coli* DNA using an IS2 Probe

Genomic DNA from various *E. coli* strains, including over 30 O157:H7 strains was cleaved with EcoRI (shown in FIGS. 6B and 7) or with EcoRV (data not shown) and fractionated on agarose gels. After transfer of the fragments to Nytran™, hybridization with the IS2 probe was carried out under stringent conditions and showed that all of the O157:H7 strains possessed a hybridizing EcoRI fragment of about 8.5 kbp (see FIGS. 6A and 7 and Table 1) and about 10 kbp EcoRV fragment (not shown). None of the other *E. coli* strains contained these fragments, even though hybridizing fragments of other sizes were detected. This result suggests that although IS2 sequences may be present in many *E. coli* strains, IS2 has integrated into genomic sequences comprising the about 8.5 kbp EcoRI and about 10 kbp EcoRV fragments that are unique to *E. coli* O157:H7, and therefore diagnostic of this strain. In other words, it is apparent that other *E. coli* strains contain IS2 sequences, but none of the other strains tested exhibited these specific hybridizing fragments observed in *E. coli* O157:H7.

Figure 6B:
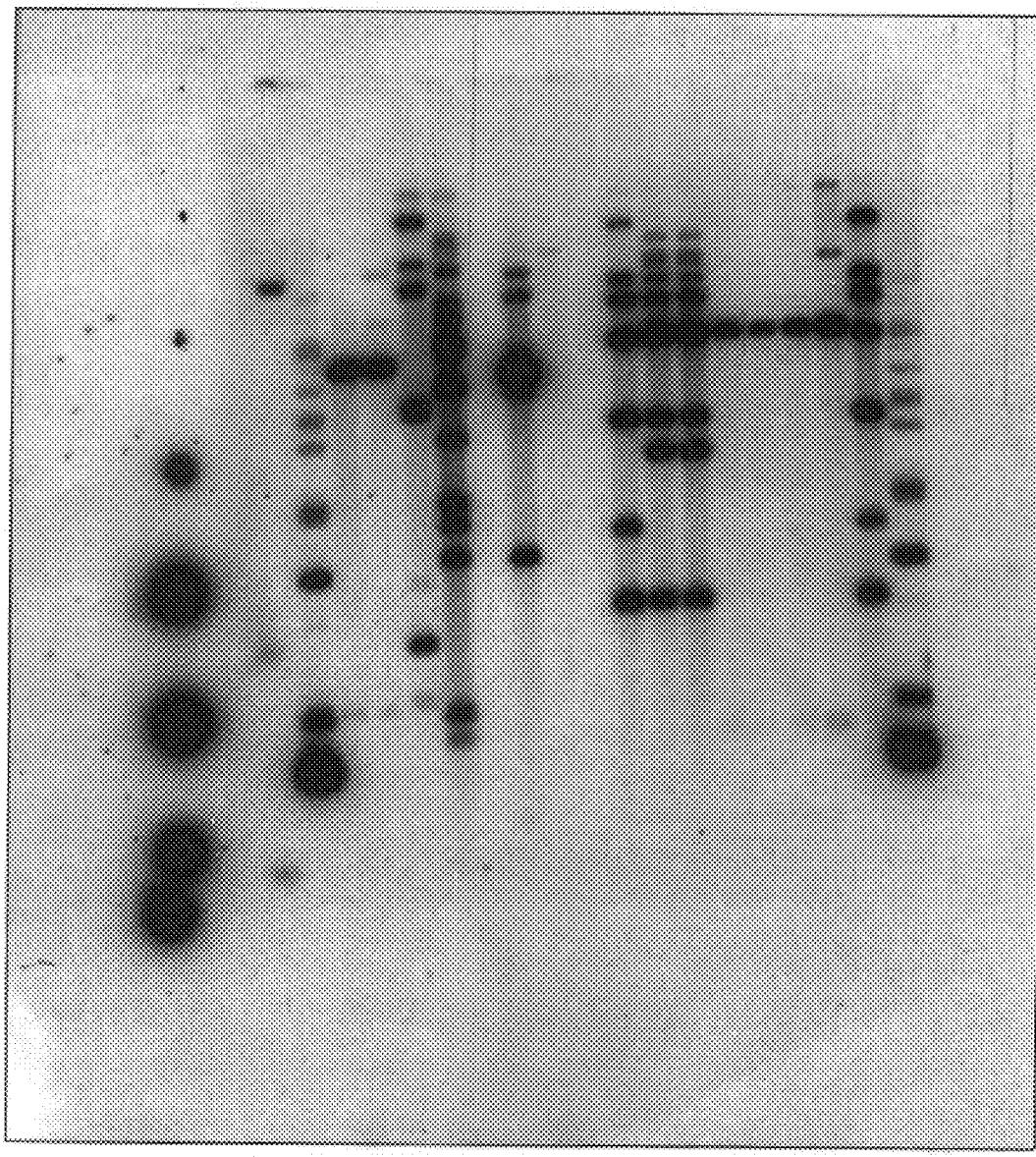
FIG. 6B shows the same Southern blot hybridized with the IS2 fragment (SEQ ID NO:3)
Figure 7:
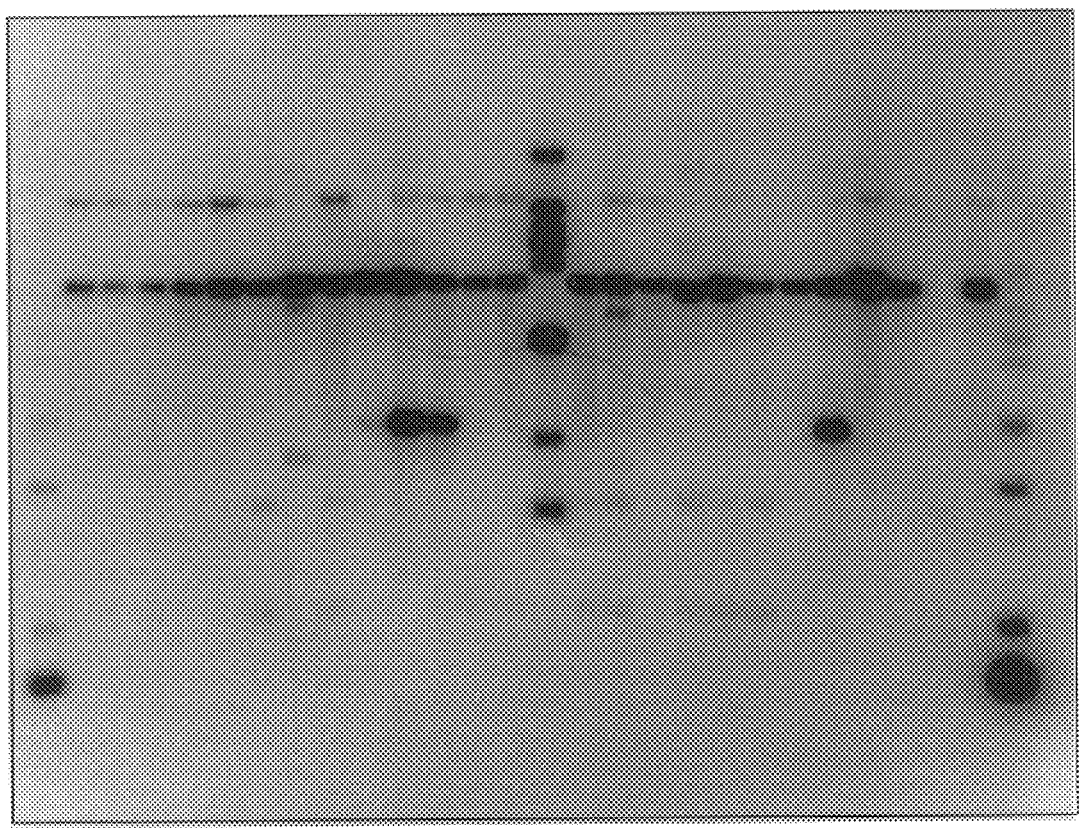
FIG. 7 shows a Southern blot of genomic DNA derived from various *E. coli* O157:H7 strains using the IS2 fragment (SEQ ID NO:3) as a probe.

The DNA samples analyzed in FIG. 6B are as already described in Example 5, but for this experiment, hybridization was carried out with a probe comprising the IS2 sequence (SEQ ID NO:3). In FIG. 7, lanes 1 and 28 represent size standards (λgal-IS2 DNA partially digested with HincII); lanes 2 through 13: AlaHD human isolates of *E. coli* O157:H7, strains 8112, 8113, 8114, 8115, 8116, 8177, 8178, 8179, 8181, 8182, 8183, 8184; lanes 14 and 16: *E. coli* O157:H7 human isolates from the ATCC, 8124 and 8127; lane 15: *E. coli* K12 strain 4717; lanes 17 through 24: human isolates of *E. coli* O157:H7 from the CDC—strains 8101, 8102, 8103, 8104, 8105, 8106, 8107, 8108; lanes 25 through 27: *E. coli* O157:H7 isolates from retail meat departments—strains 7327, 7329, 7331.

To further characterize the sequences flanking the IS2 element in the about 8.5 kbp EcoRI fragment, IPCR was carried out as described in Example 6 and the nucleotide sequence of the regions flanking IS2 were determined from outwardly facing primers that anneal within the IS2 element. The left and right flanking sequences determined in the experiments above are represented by SEQ ID NO:4 and SEQ ID NO:5, respectively.

EXAMPLE 9

Diagnostic PCR of O157:H7 Strains

Figure 8:
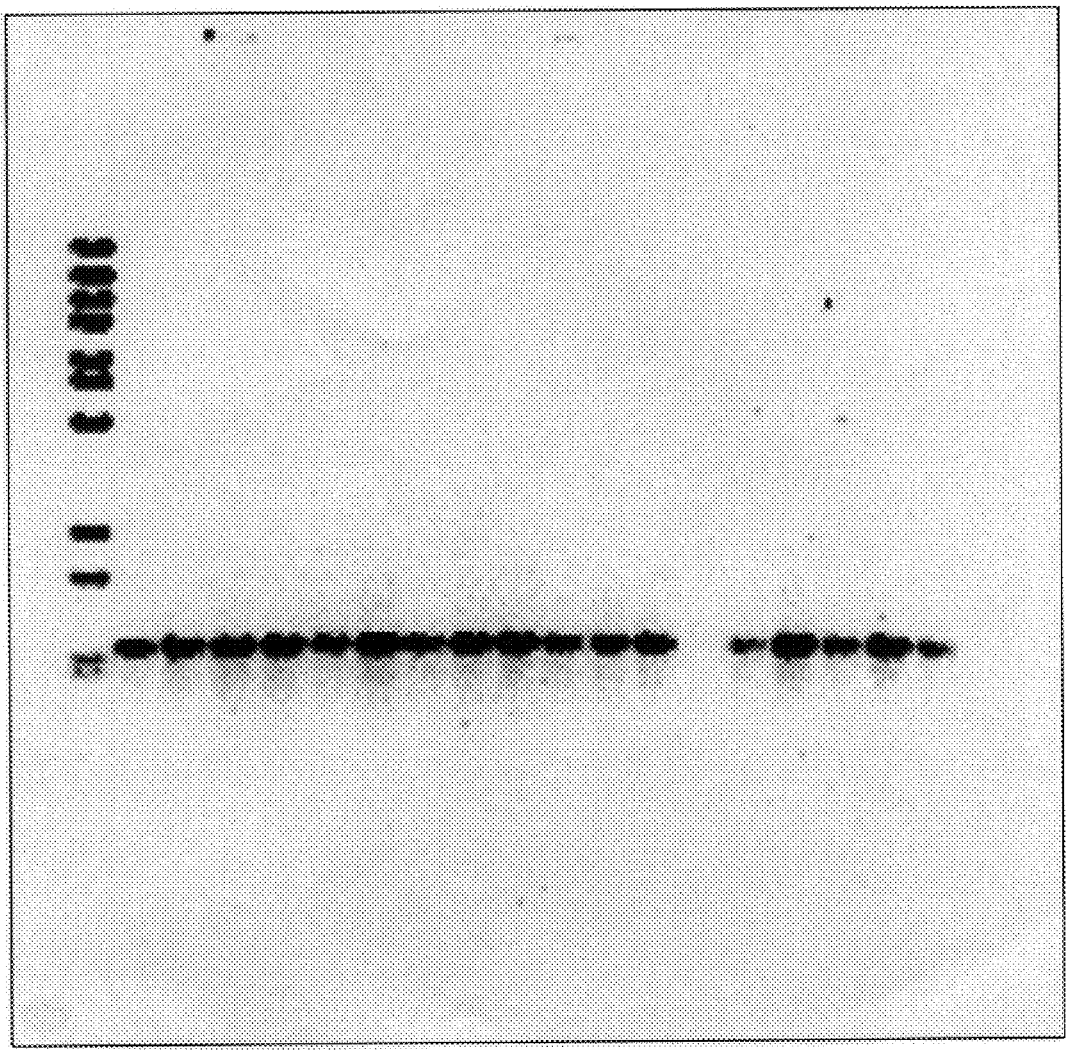
FIG. 8 shows the PCR products obtained from various O157:H7 strains using primers N63 (SEQ ID NO:6) and N64 (SEQ ID FIG. 9 shows a Southern blot of various O157:H7 strains using simultaneously both the IS2 and 441 bp fragments as probes.

Based upon the left and right flanking sequences determined in Example 7, oligonucleotide primers N63 and N64 (SEQ ID NO:6 and SEQ ID NO:7, respectively) were synthesized which anneal to the regions flanking IS2 within the about 8.5 kbp EcoRI fragment. These primers target the sequences flanking the characteristic IS2 element in *E. coli* O157:H7; amplification of the IS2 and flanking sequences produces a amplicon of ~1.4 kb, as shown in FIG. 8. Lane 1 represents the λ BstEII standard; reactions for lanes 2 through 19 had template from the following isolates of *E. coli* O157:H7: 8429, 8431, 8432, 8433, 8434, 8435, 8436, 8437, 8438, 8439, 8441, 8442, 8443, 8444, 8445, 8446, and 8447; lane 20 represents the *E. coli* K12 strain, 4789. As shown in FIG. 8 and in Table 1, PCR reactions utilizing these primers produced a product of 1.4 kbp in O157:H7 strains, but not in other *E. coli* strains nor in other bacteria. This results indicates that these primers are specific for O157:H7 strains. Reactions that utilize an outwardly directed primer that anneals within the IS2 sequence (SEQ ID NO:3) and an inwardly directed primer that anneals to the sequences which flank on the right or left sides of the IS2 sequence (SEQ ID NO:4 or SEQ ID NO:5, respectively) are also diagnostic for *E. coli* O157:H7. For example, a primer pair comprising SEQ ID NO:6 and a primer that anneals to the IS2 sequence (SEQ ID NO:3) generates a diagnostic product of 120 bp comprising the right end of the IS2 sequence (SEQ ID NO:3) and at least a portion of the right flanking sequence, and the primer pair comprising SEQ ID NO:7 and a primer that anneals to the IS2 sequence (SEQ ID NO:3) generates a diagnostic product of 160 bp comprising the left end of the IS2 sequence (SEQ ID NO:3) and at least a portion of the left flanking sequence.

EXAMPLE 10

Simultaneous Multiple Diagnostic Test for O157:H7 Strains

Since the diagnostic tests described in the preceding examples appear to detect two distinct unique regions of the O157:H7 genome (i.e., the 441 bp sequence and the IS2 flanking regions), conducting the two tests simultaneously on a given sample will yield an even more specific test for O157:H7 strains. As shown in FIG. 9, Southern blots of various O157:H7 strains using both the 440 bp probe and the IS2 probe simultaneously identified the about 8.5 kbp and 7.5 kbp EcoRI fragments in all samples. Lanes 1 and 28: standard (λ-gal-IS2 DNA partially digested with HincII); lanes 2 through 13: AlaHD human isolates of *E. coli* O157:H7, strains 8112, 8113, 8114, 8115, 8116, 8177, 8178, 8179, 8181, 8182, 8183, 8184; lanes 14 and 16: *E. coli* O157:H7 human isolates from the ATCC, 8124 and 8127; lane 15: *E. coli* K12 strain 4717; lanes 17 through 24: human isolates of *E. coli* O157:H7 from the CDC—strains 8101, 8102, 8103, 8104, 8105, 8106, 8107, 8108; lanes 25 through 27: *E. coli* O157:H7 isolates from retail meat departments— strains 7327, 7329, 7331.

In addition, PCR reactions with primers N58 (SEQ ID NO:2), N63 (SEQ ID NO:6), and N64 (SEQ ID NO:7) also yielded both expected PCR products, i.e., the 0.4 kbp N58 (SEQ ID NO:2) fragment and the 1.4 kbp IS2 fragment (not shown).

TABLE I

Bacterial Strains and Results

| REM | Source[B] | Product[A]: | 0.4 kb by PCR (N58) | 1.4 kb by PCR (N63/N64) | 7.5 kb by Southern (441bp) | 8.5 kb by Southern (IS2) |
|---|---|---|---|---|---|---|
| *E. coli* O157:H7 Isolates (* designates weak reaction with anti-H7 antibody) | | | | | | |
| 7327 | M. Doyle | (301C) | + | + | + | + |
| 7329 |  | (204P) | + | − | + | − |
| 7331 |  | (505B) | + | + | + | + |
| 8124 | ATCC | (35150) | + | + | + | + |
| 8127 |  | (43895) | + | + | + | + |
| 8186 |  | (43894) | + | + | + | + |
| 8101 | CDC | (A7793) | + | + | + | + |
| 8102 |  | (131409) | + | + | + | + |
| 8103 |  | (136903) | + | − | + | − |
| 8104 |  | (136914) | + | + | + | + |
| 8105 |  | (138763) | + | + | + | + |
| 8106 |  | (C4193) | + | + | + | + |
| 8107 |  | (C8958) | + | + | + | + |
| 8108 |  | (C9490) | + | + | + | + |
| 8112 | AlaHD | (38) | + | + | + | + |
| 8113 |  | (44) | + | + | + | + |
| 8114 |  | (497) | + | + | + | + |
| 8115 |  | (505) | + | + | + | + |
| 8116 |  | (506) | + | + | + | + |
| 8177 |  | (341) | + | + | + | + |
| 8178 |  | (364) | + | + | + | + |
| 8179 |  | (434) | + | + | + | + |
| 8181 |  | (436) | + | + | + | + |
| 8182 |  | (491) | + | + | + | + |
| 8183 |  | (494) | + | + | + | + |
| 8184 |  | (576) | + | + | + | + |
| 8118 | AUVM | (6247-11-95) | + | + | + | + |

TABLE I-continued

Bacterial Strains and Results

| REM | Source[B] | Product[A]: | 0.4 kb by PCR (N58) | 1.4 kb by PCR (N63/N64) | 7.5 kb by Southern (441bp) | 8.5 kb by Southern (IS2) |
|---|---|---|---|---|---|---|
| 8138 | | (6244-12-95) | + | + | + | + |
| 8139 | | (6246-12-95) | + | + | + | + |
| 8141 | | (6247-12-95) | + | + | + | + |
| 8142 | | (6283-12-95) | + | + | + | + |
| 8143 | | (6284-1-96) | + | + | + | + |
| 8144 | | (6316-1-96) | + | + | + | + |
| 8171 | | (C11-1) | + | + | + | + |
| 8172 | | (C11-2) | + | + | nt | nt |
| 8173* | | (C12-3) | + | + | + | + |
| 8174* | | (C11A) | + | + | nt | nt |
| 8175 | | (C40-1) | + | + | + | + |
| 8176* | | (C20) | + | + | + | + |
| 8145 | Mathewson | | + | + | + | + |
| 8412 | TexHD | (A60) | + | + | No Southern Analyses done for any isolate from TexHD | |
| 8413 | | (A61) | + | + | | |
| 8414 | | (A62) | + | + | | |
| 8416 | | (A64) | − | + | | |
| 8417 | | (A65) | + | + | | |
| 8418 | | | + | + | | |
| 8419 | | | + | + | | |
| 8421 | | (A68) | + | + | | |
| 8422 | | | + | + | | |
| 8423 | | | + | + | | |
| 8424 | | | − | + | | |
| 8425 | | | − | + | | |
| 8426 | | | + | + | | |
| 8427 | | | + | + | | |
| 8428 | | | − | + | | |
| 8429 | | | − | + | | |
| 8431 | | (A77) | − | + | | |
| 8432 | | | − | + | | |
| 8433 | | | + | + | | |
| 8434 | | | + | + | | |
| 8435 | | | + | + | | |
| 8436 | | | + | + | | |
| 8437 | | | − | + | | |
| 8438 | | | + | + | | |
| 8439 | | | + | + | | |
| 8441 | | (A86) | + | + | | |
| 8442 | | | + | + | | |
| 8443 | | | + | − | | |
| 8444 | | | + | + | | |
| 8445 | | | + | + | | |
| 8446 | | | + | + | | |
| 8447 | | | + | + | | |
| 8448 | | | + | + | | |
| 8449 | | | + | + | | |
| 8451 | | (A95) | + | + | | |
| 8452 | | | + | − | | |
| 8453 | | | + | + | | |
| 8454 | | | + | + | | |
| 8455 | | | + | + | | |
| 8456 | | | + | − | | |
| 8457 | | | + | + | | |
| 8458 | | | − | + | | |
| 8459 | | | − | − | | |
| 8461 | | (A104) | + | + | | |
| 8462 | | (A105) | + | + | | |
| 8463 | | | − | + | | |
| 8464 | | | + | + | | |
| 8465 | | | + | + | | |
| 8466 | | | + | − | | |
| 8467 | | | + | + | | |
| 8468 | | | + | + | | |
| 8469 | | (A112) | + | + | | |
| 8185 | J.Shaw | (8186 wo/pO157) | + | + | + | + |
| Other E. coli Strains | | | | | | |
| 0489 | E. coli K12/Casadaban (MC1061) | | − | − | − | − |
| 4717 | E. Coli K12/ATCC (12435) (W1485) | | − | − | − | − |
| 4789 | E. Coli K12/Bachmann (M01655) | | − | − | − | − |
| 8109 | E. coli K12 (SLT-I)/CDC (C600:933J) | | − | − | nt | nt |
| 8111 | E. colI K12 (SLT-II)/CDC (C600:933W) | | − | − | nt | nt |
| 0889 | E. coli C/Donier (C1a) | | − | − | − | − |

TABLE I-continued

Bacterial Strains and Results

| REM | Source[B] | Product[A]: 0.4 kb by PCR (N58) | 1.4 kb by PCR (N63/N64) | 7.5 kb by Southern (441bp) | 8.5 kb by Southern (IS2) |
|---|---|---|---|---|---|
| 0901 | E. coli B/Donier | − | − | nt | − |
| 5529 | E. coli ML/ATCC (15223) | − | − | nt | − |
| 4724 | E. coli W/ATCC (9637) | − | − | nt | − |
| 7328 | E. coli./M. Doyle (IP) | − | − | nt | − |
| 8117 | E. coli/AUVM (6067-7-95) | − | − | nt | nt |
| 8121 | E. coli/J. Barbaree (25922) | − | − | nt | nt |
| 8415 | E. coli/TexHD (A63) | − | − | nt | nt |
| 8381 | E. coli/AUVM (C20-LP) | − | − | − | − |
| 8382 | E. coli/AUVM (43-SP) | − | − | − | − |
| 8383 | E. coli/AUVM (37-1) | − | − | − | − |
| 8384 | E. coli/AUVM (37-3) | − | − | − | − |
| 8385 | E. coli/AUVM (41-4) | − | − | − | − |
| 8386 | E. coli/AUVM (43-1) | − | − | − | − |
| 8387 | E. coli/AUVM (434) | − | − | − | − |
| 8388 | E. coli/AUVM (54-2) | − | − | − | − |
| 8389 | E. coli/AUVM (54-3) | − | − | − | − |
| 8379 | E. coli (STb)/NADC (1790) | − | − | − | nd |
| 8471 | E. coli O26:H11/BAF (658) | − | − | − | − |
| 8472 | E. coli O112:NM/BAF (659) | − | − | − | − |
| 8473 | E. coli O18ab:K76(B20):H14/BAF (660) | − | − | − | − |
| 8474 | E. coli O111:H12/BAF (682) | − | − | − | − |
| 8475 | E. coli O55:H7/BAF (689) | − | − | − | − |
| 8476 | E. coli O126:B16/CDC (6375-59) | − | − | − | − |
| 8146 | E. coli/BAF (6459) | − | − | The following E. coli isolates were not tested by Southern Hybridization. | |
| 8147 | E. coli/BAF (15597) | − | − | | |
| 8148 | E. coli/BAF (88) | − | − | | |
| 8149 | E. coli/BAF (189) | − | − | | |
| 8151 | E. coli/BAF (194) | − | − | | |
| 8152 | E. coli/BAF (221) | − | − | | |
| 8153 | E. coli/BAF (2252) | − | − | | |
| 8154 | E. coli/BAF (2287) | − | − | | |
| 8155 | E. coli/BAF (2295) | − | − | | |
| 8156 | E. coli/BAF (2296) | − | − | | |
| 8157 | E. coli/BAF (M3N) | − | − | | |
| 8158 | E. coli/BAF (M3P) | − | − | | |
| 8159 | E. coli/BAF (M28) | − | − | | |
| 8161 | E. coli/BAF (M51H) | − | − | | |
| 8162 | E. coli/BAF (M51M) | − | − | | |
| 8163 | E. coli/BAF (M388) | − | − | | |
| 8164 | E. coli/BAF (MD4) | − | − | | |
| 8165 | E. coli/BAF (N2RR) | − | − | | |
| 8166 | E. coli/BAF (N4B) | − | − | | |
| 8167 | E. coli/BAF (SM36) | − | − | | |
| 8168 | E. coli/BAF (V517) | − | − | | |
| | Other Bacterial strains | | | | |
| 5532 | Escherichia blattae/ATCC (29907) | − | − | nt | − |
| 8131 | E. fergusonii/ATCC (35469) | − | − | nt | − |
| 8134 | E. hermannii/ATCC (33650) | − | − | nt | − |
| 8478 | E. hermannii/BAF (1200) | − | − | nt | − |
| 8137 | E. vulneris/ATCC (33821) | − | − | nt | − |
| 8477 | E. vulneris/BAF (1168) | − | − | nt | − |
| 4726 | Shigella boydii/ATCC (29928) | − | − | nt | nd |
| 4728 | S. boydii serotype 1/ATCC (9207) | − | − | − | nd |
| 8345 | S. boydii type 2/ATCC (8706) | − | − | | |
| 8346 | S. boydii type 3/ATCC (9209) | − | − | | |
| 8347 | S. boydii type 4/ATCC (9210) | − | − | | |
| 2105 | S. dysenteriae/S. Baer | | | − | nd |
| 2125 | S. dysenteriae(P2)/ATCC (11456b) | − | − | − | nd |
| 8341 | S. dysenteriae type 1/ATCC (9361) | − | − | nt | nd |
| 8342 | S. dysenteriae type 2/ATCC (9750) | − | − | | |
| 8343 | S. dysenteriae type 3/ATCC (9751) | − | − | | |
| 8344 | S. dysenteriae type 5/ATCC (9764) | − | − | | |
| 3577 | S. flexneri/R. Lawther (53-B) | | | − | − |
| 3578 | S. flexneri/R. Lawther (7341) | | | − | |
| 8348 | S. flexneri type 1b/ATCC (9380) | − | − | nt | nd |
| 8349 | S. flexneri type 2a/ATCC (9473) | − | − | | |
| 4731 | S. flexneri type 2b/ATCC (12022) | − | − | − | nd |
| 8351 | S. flexneri type 3/ATCC (9403) | − | − | | |
| 8352 | S. flexneri type 4a/ATCC (12023) | − | | | |
| 3576 | S. sonnei/R. Lawther (53-1) | nt | − | | |
| 3577 | S. sonnei/R. Lawther (16) | − | − | | |
| 4733 | S. sonnei/ATCC (9290) | − | − | nt | nd |
| 8371 | S. sonnei colicin indicator I1/BAF (1121) | − | − | nt | nd |

TABLE I-continued

Bacterial Strains and Results

| REM | Source[B] | Product[A]: 0.4 kb by PCR (N58) | 1.4 kb by PCR (N63/N64) | 7.5 kb by Southern (441bp) | 8.5 kb by Southern (IS2) |
|---|---|---|---|---|---|
| 8373 | S. sonnei colicin indicator I3/BAF (1123) | − | − | | |
| 8374 | S. sonnei colicin indicator I4/BAF (1124) | − | − | | |
| 8375 | S. sonnei colicin indicator I8/BAF (1128) | − | − | | |
| 2106 | Salmonella typhimurium/S. Baer | | | | |
| 2119 | S. typhimurium LT2/ATCC (23564) | − | nt | nt | − |

[A]Results are expressed as:
+ means the characteristic product was detected
− means the characteristic product was not detected
nt means not tested, also if left blank.
nd means not determinable: Shigella spp. generally have over 20 copies of IS2 so it cannot be reliable determined whether the 8.5 kb band characteristic of E. coli O157:H7 is present; this also applies to the E. coli strain REM 8379.
[B]Sources for the strains are indicated by the name of the individual donor or by the institution, abbreviated as ATCC (American Type Culture Collection), CDC (Center for Disease Control and Prevention, via J. Barbaree), AlaHD (Alabama State Health Department, via J. Barbaree), TexHD (Texas State Health Department, via J. Shaw), AUVM (Auburn University College of Veterinary Medicine, via S. Price), NADC (National Animal Disease Center), and BAF (Brooks Air Force Base, via J. Shaw).

---

What is claimed is:

1. An isolated DNA fragment consisting of SEQ ID NO:13 or a fragment thereof comprising at least 24 consecutive bases of the DNA sequence shown in SEQ ID NO:13.

2. The isolated DNA fragment of claim 1 comprising SEQ ID NO:13.

3. A method for detecting *E. coli* O157:H7 in a sample, comprising obtaining DNA from said sample, amplifying said DNA using a polymerase chain reaction, and testing said amplified DNA to determine the presence or absence of a DNA sequence comprising at least 12 consecutive nucleotides of the nucleotide sequence of SEQ ID NO:3 and at least one additional nucleotide sequence selected from the group consisting of SEQ ID NO:4 and SEQ ID NO:5 in said amplified DNA, wherein the presence of said DNA sequence is indicative of the presence of *E. coli* O157:H7 in said sample, thereby detecting said *E. coli* O157:H7 in said sample.

4. The method of claim 3 wherein said polymerase chain reaction uses as primers a first nucleotide sequence that specifically anneals to SEQ ID NO:3 and a second nucleotide sequence that specifically anneals to a nucleotide sequence selected from the group consisting of SEQ ID NO:4 and SEQ ID NO:5.

5. The method of claim 4 wherein said polymerase chain reaction comprises at least one primer selected from the group consisting of SEQ ID NO:6 and SEQ ID NO:7.

6. The method of claim 3 wherein said polymerase chain reaction comprises a first primer and a second primer, wherein said first primer specifically anneals to SEQ ID NO:4 and said second primer specifically anneals to SEQ ID NO:5.

7. The method of claim 6 wherein said first primer comprises SEQ ID NO:6 and said second primer comprises SEQ ID NO:7.

8. The method of claim 7 wherein said polymerase chain reaction produces a fragment of 1.4 kbp.

9. A method for detecting E. coli O157:H7 in a sample, comprising obtaining DNA from said sample; annealing said DNA with a nucleotide probe comprising at least a portion of SEQ ID NO:3, wherein said portion specifically hybridizes to SEQ ID NO:3, and comprising at least one second sequence comprising a nucleotide sequence selected from the group consisting of SEQ ID NO:4 and SEQ ID NO:5, thereby forming annealed probe; and detecting said annealed probe, wherein the presence of said annealed probe is indicative of the presence of E. coli O157:H7 in said sample, thereby detecting said E. coli O157:H7 in said sample.

10. The method of claim 9 further comprising an additional step of digesting said DNA of said sample with at least one restriction enzyme prior to annealing said DNA with said nucleotide probe.

11. The method of claim 10 wherein said restriction enzyme is selected from the group consisting of EcoRI and EcoRV.

12. The method of claim 11 wherein said restriction enzyme is EcoRI, and wherein said probe anneals to a fragment of about 8.5 kbp.

13. The method of claim 11 wherein said restriction enzyme is EcoRV, and wherein said probe anneals to a fragment of about 10 kbp.

14. An isolated DNA fragment comprising at least a portion of the nucleotide sequence of SEQ ID NO:3, and a sequence selected from the group consisting of SEQ ID NO:4, SEQ ID NO:5, SEQ ID NO:6, and SEQ ID NO:7, wherein said fragment specifically hydridizes to E. coli O157:H7 nucleic acids.

15. An oligonucleotide primer up to 30 nucleotides in length comprising a nucleotide sequence selected from the group consisting of SEQ ID NO:6, SEQ ID NO:7, SEQ ID NO:9, SEQ ID NO:10 SEQ ID NO:14, and SEQ ID NO:15.

16. An isolated restriction fragment comprising at least a 12 mer segment of the nucleotide sequence of SEQ ID NO:3, which 12 mer segment specifically hybridizes to E. coli O157:H7 nucleic acids.

17. The restriction fragment of claim 16 wherein said restriction fragment is about 8.5 kbp.

18. The restriction fragment of claim 16 wherein said restriction fragment is about 10 kbp.

19. An isolated restriction fragment comprising at least a 12 mer segment of the nucleotide sequence of SEQ ID NO:3, wherein said fragment is obtained by digesting E. coli O157:H7 DNA with a restriction enzyme selected from the group consisting of EcoRI and EcoRV.

20. An isolated restriction fragment comprising at least a 12 mer segment of the nucleotide sequence of SEQ ID NO:3, further comprising additional nucleotide sequences flanking said at least a 12 mer segment, which additional nucleotide sequences comprise a nucleotide sequence selected from the group consisting of SEQ ID NO:4 and SEQ ID NO:5.

21. A 1.4 kbp amplicon obtained by specifically amplifying E. coli O157:H7 DNA with oligonucleotide primers, wherein said primers comprise SEQ ID NO:6 and SEQ ID NO:7, and wherein said primers specifically hybridize to said E. coli O157:H7 DNA.

22. A kit for detecting E. coli O157:H7 in a sample, comprising oligonucleotide primers which specifically anneal to and specifically amplify at least a portion of a nucleotide sequence comprising SEQ ID NO:13, wherein said portion comprises at 24 consecutive nucleotides of SEQ ID NO:13, a positive control DNA comprising E. coli O157:H7 genomic DNA, negative control DNA comprising E. coli K12 genomic DNA, and instructions for use.

23. The kit of claim 22 wherein said oligonucleotide primers comprise an oligonucleotide comprising SEQ ID NO:2.

24. The kit of claim 23 further comprising a size reference for an expected polymerase chain reaction product generated using SEQ ID No. 2, and wherein said oligonucleotide primers comprise an oligonucleotide comprising the sequence of SEQ ID NO:8.

25. A kit for detecting E. coli O157:H7 in a sample, comprising isolated DNA fragments consisting of SEQ ID NO:1 or SEQ ID NO:13, positive control DNA comprising E. coli O157:H7 genomic DNA, negative control DNA comprising E. coli K12 genomic DNA and instructions for use.

26. A kit for detecting E. coli O157:H7 in a sample, comprising
  at least one pair of primers selected from the group consisting of SEQ ID NO:6 and SEQ ID NO:7, SEQ ID NO:6 and a primer that specifically anneals to SEQ ID NO:3, and SEQ ID NO:7 and a primer that specifically anneals to SEQ ID NO:3;
  positive control DNA comprising E. coli O157:H7 genomic DNA;
  negative control DNA comprising E. coli K12 genomic DNA; and instructions for use.

27. A kit for detecting E. coli O157:H7 in a sample, comprising isolated DNA fragments consisting of SEQ ID NO:3, SEQ ID NO:4, and SEQ ID NO:5, positive control DNA comprising E. coli O157:H7 genomic DNA, negative control DNA comprising E. coli K12 genomic DNA, and instructions for use.

28. A method for detecting E. coli O157:H7 in a sample comprising obtaining DNA from said sample, determining the presence or absence of a nucleotide sequence comprising SEQ ID NO:13 or at least a 24 mer segment thereof that specifically hybridizes to E. coli O157:H7 nucleic acids in said DNA of said sample, wherein the presence of said nucleotide sequence is indicative of the presence of E. coli O157:H7 in said sample, thereby detecting said E. coli O157:H7 in said sample.

29. The method of claim 28 wherein said presence or absence of said nucleotide sequence comprising SEQ ID NO:13 or at least a 24 mer segment thereof is determined using a polymerase chain reaction.

30. The method of claim 29 wherein said polymerase chain reaction is performed with only one primer.

31. The method of claim 30 wherein said polymerase chain reaction is performed at an annealing temperature of about 42° C. and an extension temperature of about 72° C.

32. The method of claim 30 wherein said polymerase chain reaction is performed at an annealing temperature of about 52° C. and an extension temperature of about 68° C.

33. The method of claim 30 wherein said primer is a polynucleotide comprising SEQ ID NO:2.

34. The method of claim 30 wherein said primer is a polynucleotide comprising SEQ ID NO:16.

35. The method of claim 28 wherein said sample is food or fecal material.

36. A method for detecting *E. coli* O157:H7 in a sample comprising obtaining DNA from said sample, digesting said DNA with at least one restriction enzyme, thereby forming digested DNA, and detecting a restriction fragment comprising at least a portion of a nucleotide sequence comprising SEQ ID NO:13 in said digested DNA of said sample, wherein said portion comprises SEQ ID NO:13 or at least a 24 mer segment thereof that specifically hybridizes to *E. coli* O157:H7 nucleic acids, and wherein the presence of said restriction fragment is indicative of the presence of *E. coli* O157:H7 in said sample, thereby detecting said *E. coli* O157:H7 in said sample.

37. The method of claim 36 wherein said at least one restriction enzyme is selected from the group consisting of EcoRI and EcoRV.

38. The method of claim 36 wherein said detecting a restriction fragment comprises contacting said digested DNA with a nucleic acid probe which is complementary in base sequence to at least said portion of the sequence comprising SEQ ID NO:13, allowing the probe to specifically anneal to the digested DNA, and detecting said digested DNA bound to the probe as indicative of the presence of said restriction fragment.

39. The method of claim 36 wherein said sample is food or fecal material.

40. The method of claim 36 wherein said detecting a restriction fragment comprises allowing a nucleotide probe which is complementary in base sequence to said portion of the nucleotide sequence comprising SEQ ID NO:13 to contact said digested DNA, wherein said probe thereby specifically anneals to said portion of the nucleotide sequence of SEQ ID NO:13, thereby forming annealed probe, and detecting said annealed probe as indicative of the presence of said restriction fragment.

41. The method of claim 40 wherein said detecting a restriction fragment is performed under high stringency conditions.

\* \* \* \* \*